US009657341B2

(12) United States Patent
Park et al.

(10) Patent No.: US 9,657,341 B2
(45) Date of Patent: May 23, 2017

(54) MICROFLUIDIC SYSTEM FOR NUCLEIC ACID ANALYSIS

(71) Applicant: Samsung Electronics Co., Ltd., Suwon-si, Gyeonggi-do (KR)

(72) Inventors: Chin-sung Park, Yongin-si (KR); Kak Namkoong, Seoul (KR); Joon-sub Shim, Yongin-si (KR); Won-seok Chung, Suwon-si (KR); Kyung-ho Kim, Seoul (KR); Joon-ho Kim, Seongnam-si (KR); Won-jong Jung, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 650 days.

(21) Appl. No.: 14/074,590

(22) Filed: Nov. 7, 2013

(65) Prior Publication Data
US 2014/0206073 A1      Jul. 24, 2014

(30) Foreign Application Priority Data
Jan. 24, 2013   (KR) .................. 10-2013-0008210

(51) Int. Cl.
*C12Q 1/68* (2006.01)
*B01L 3/00* (2006.01)
*B01L 7/00* (2006.01)

(52) U.S. Cl.
CPC .......... *C12Q 1/686* (2013.01); *B01L 3/5027* (2013.01); *B01L 7/525* (2013.01);
(Continued)

(58) Field of Classification Search
CPC .. G01P 15/125; G01P 15/18; B01L 2200/025; B01L 2220/028;
(Continued)

(56) References Cited

FOREIGN PATENT DOCUMENTS

KR       1000839585 B1    6/2008
KR      1020120062265 A    6/2012
(Continued)

*Primary Examiner* — Nathan Bowers
*Assistant Examiner* — Lydia Edwards
(74) *Attorney, Agent, or Firm* — Leydig, Voit & Mayer, Ltd.

(57) ABSTRACT

A microfluidic system for analyzing nucleic acid, the microfluidic system including a reagent supply device including a sample chamber into which a sample can be injected, one or more reagent chambers for containing one or more reagents for extracting nucleic acid from the sample, and a waste chamber in which the used reagent can be discarded; a binding-lysis chamber in which cells are captured from the sample and lysed to form a cell lysate containing nucleic acid; plurality of particles for cell binding disposed in the binding-lysis chamber; a plurality of rehydration chambers into which the cell lysate formed in the binding-lysis chamber can be distributed and mixed with a nucleic acid amplification reagent to form an amplification reaction mixture; a plurality of amplification chambers in which a nucleic acid amplification reaction is performed on the amplification reaction mixture introduced from the plurality of rehydration chambers; and a flow channel system including an outlet and a plurality of inlets connected to the reagent supply device and forming an integrated fluid flow between the binding-lysis chamber, the rehydration chambers, and the amplification chambers.

31 Claims, 26 Drawing Sheets

(52) U.S. Cl.
CPC ... *B01L 2200/025* (2013.01); *B01L 2200/028* (2013.01); *B01L 2200/0684* (2013.01); *B01L 2200/10* (2013.01); *B01L 2300/0672* (2013.01); *B01L 2300/0816* (2013.01); *B01L 2300/0864* (2013.01); *B01L 2300/0867* (2013.01); *B01L 2400/0487* (2013.01); *B01L 2400/0655* (2013.01); *B01L 2400/0683* (2013.01); *B01L 2400/086* (2013.01)

(58) Field of Classification Search
CPC ......... B01L 2200/0684; B01L 2200/10; B01L 2300/0672; B01L 2300/0816; B01L 2300/0864; B01L 2300/0867; B01L 2400/0487; B01L 2400/0655; B01L 3/5027; B01L 7/525; C12Q 1/686
See application file for complete search history.

(56) References Cited

FOREIGN PATENT DOCUMENTS

| | | |
|---|---|---|
| KR | 1020120063162 A | 6/2012 |
| KR | 1020120086087 A | 8/2012 |

M1~M6   R1~R6   P1~P6

M1~M6   R1~R6   P1~P6

MICROFLUIDIC SYSTEM FOR NUCLEIC ACID ANALYSIS

CROSS-REFERENCE TO RELATED APPLICATIONS

This application claims the benefit of Korean Patent Application No. 10-2013-0008210, filed on Jan. 24, 2013 in the Korean Intellectual Property Office, the entire disclosure of which is hereby incorporated by reference.

BACKGROUND

1. Field

The present disclosure relates to microfluidic systems for conducting cell binding, lysis, nucleic acid extraction, and amplification.

2. Description of the Related Art

The importance of genetic analysis, in vitro diagnostics, and gene sequencing has been emphasized in line with the emerging era of point-of-care diagnostics, and demand, therefore, continues to gradually increase. Recently, because accuracy and sensitivity of molecular diagnostic methods based on nucleic acid are excellent, utilization thereof in relation to infectious diseases, cancer diagnostics, and pharmacogenomics has considerably increased.

Meanwhile, in order to accurately identify the presence of particular deoxyribonucleic acid ("DNA") and an amount of DNA in a sample, a process of sufficiently amplifying nucleic acid is required so as to measure the nucleic acid after purification/extraction of an actual sample. For example, a polymerase chain reaction ("PCR") is the most widely used method among various gene amplification methods. A process of capturing cells from a biological sample, a process of extracting nucleic acid through cell lysis, and a process of mixing the nucleic acid with a PCR reagent may be carried out in order to perform the PCR.

SUMMARY

Provided are microfluidic systems capable of conducting a series of processes of capturing cells in a sample, extracting nucleic acid by lysis of the captured cells, and performing a nucleic acid amplification reaction in a single device. Additional aspects will be set forth in the description which follows and will be apparent from the description, or may be learned by practice of the presented embodiments.

According to an aspect of the present invention, a microfluidic system for analyzing nucleic acid includes: a reagent supply device including a sample chamber in which a sample as an examination target is injected, a plurality of reagent chambers in which a reagent for extracting nucleic acid from the sample is injected, and one or more waste chambers in which the used reagent is discarded; a binding-lysis chamber in which cells are captured from the sample and lysed to form a cell lysate containing nucleic acid, and in which a plurality of particles for cell binding are disposed; a plurality of rehydration chambers in which the cell lysate formed in the binding-lysis chamber is distributed and introduced, each rehydration chamber containing a nucleic acid amplification reagent that is mixed with the introduced cell lysate to form an amplification reaction mixture; a plurality of amplification chambers in which a nucleic acid amplification reaction is performed on the amplification reaction mixture introduced from the plurality of rehydration chambers; and a flow channel system including an outlet and a plurality of inlets connected to the reagent supply device and forming an integrated fluid flow between the binding-lysis chamber, the rehydration chambers, and the amplification chambers.

The one or more reagent chambers may include a lysis buffer chamber in which a lysis buffer is injected and a washing buffer chamber in which a washing buffer is injected.

A destruction pattern may be formed on each bottom surface of the sample chamber, the lysis buffer chamber, and the washing buffer chamber. The destruction chamber is breachable or rupturable by an external impact to discharge an injected solution from the chamber. The plurality of inlets of the flow channel system may have the shape of a needle for breaching or rupturing the destruction pattern. The destruction pattern may also be formed on a bottom surface of the waste chamber, and the outlet of the flow channel system may have the shape of a needle for breaching or rupturing the destruction pattern.

The microfluidic system for analyzing nucleic acid may further include one or more metering chambers for quantifying an amount of reagent from one or more of the reagent chambers (e.g., the lysis buffer supplied from the lysis buffer chamber and/or washing buffer from the washing buffer chamber) of the reagent supply device.

The microfluidic system for analyzing nucleic acid may further include one or more bubble trap chambers for removing bubbles generated in the binding-lysis chamber during cell lysis.

The diameters of the particles prepared in the binding-lysis chamber may be in the range of about 1 μm to about 1000 μm, and an amount of the particle may be in the range of about 1 mg to about 100 mg.

Each of the plurality of rehydration chambers may include two separated subchambers and the nucleic acid amplification reagent may be divided and disposed in the two subchambers. In each of the plurality of rehydration chambers, a sample including a nucleic acid may be disposed in one subchamber and a reagent including an enzyme may be disposed in the other subchamber. The sample including a nucleic acid may further include one or more of a probe and a primer. The nucleic acid amplification reagent may be in a freeze-dried form. A side of the subchamber may have a curved shape and a width of a flow path therethrough, by which a cell lysate is introduced, may be the smallest at a center portion of the chamber.

The microfluidic system for analyzing a nucleic acid may further include a plurality of metering chambers for quantifying an amount of the cell lysate formed in the binding-lysis chamber and for distributing the cell lysate into the plurality of rehydration chambers.

The microfluidic system for analyzing nucleic acid may include: a fluid flow part in which the inlets and the outlet connected to the reagent supply device are formed on a top surface thereof, the fluid flow part including a first through hole forming a port to the binding-lysis chamber, a plurality of second through holes forming ports to the plurality of rehydration chambers, and a recessed groove pattern on a bottom surface thereof for forming spaces of the plurality of nucleic acid amplification chambers; a membrane part bonded to the bottom surface of the fluid flow part to form bottom surfaces of the binding-lysis chamber and of the plurality of rehydration chambers, the membrane part formed of an elastic material; and a pneumatic part bonded to a bottom surface of the membrane part, the pneumatic part having a plurality of ports for applying pneumatic pressure at a predetermined position of the membrane part formed in the pneumatic part.

A microchannel for implementing the flow channel system and a microvalve for preventing flow of a fluid passing along the microchannel by pneumatic pressure applied from the pneumatic part may be formed on the bottom surface of the fluid flow part.

A plurality of particles for cell binding may be disposed in the first through hole of the fluid flow part and a particle cover covering the first through hole may be included.

The microfluidic system for analyzing nucleic acid may further include a rehydration cover covering the plurality of second through holes of the fluid flow part, wherein a plurality of protrusions is formed at positions corresponding to the plurality of second through holes, a plurality of grooves recessed in a predetermined shape is formed on the plurality of protrusions, and the nucleic acid amplification reagent in a freeze-dried state is disposed in the grooves. The diameters of the protrusions may be formed to be larger than the diameters of the second through holes, and sealing of the groove may be performed by inserting the protrusions into the second through holes.

Each of the plurality of grooves may include two subgrooves separated from each other, and the nucleic acid amplification reagent may be divided and disposed in the two subgrooves. In each of the plurality of grooves, a sample including nucleic acid may be disposed in one subgroove and a reagent including an enzyme may be disposed in the other subgroove. The sample including nucleic acid may include one or more of a probe and a primer. A side of the subgroove may have a curved shape and have a smallest width at a center portion thereof. An external angle formed by corners of both sides of the subgroove at a position having the narrowest width may be in a range of about 30 degrees to about 90 degrees.

The microfluidic system for analyzing nucleic acid may further include a PCR film forming a bottom surface of the nucleic acid amplification chamber and covering the groove pattern recessively formed on the bottom surface of the fluid flow part. A bridge pattern having a shape recessed from the top surface of the fluid flow part may be formed on the top surface of the fluid flow part, the shape forming a path in which the amplification reaction mixture formed in the rehydration chamber is transferred to the nucleic acid amplification chamber. The bridge pattern may include a plurality of subpatterns, and each of the plurality of subpatterns may be formed by including a hole penetrating the fluid flow part to face the membrane part, a hole penetrating the fluid flow part to face the PCR film, and a recessed bridge groove connecting the two holes on the top surface of the fluid flow part. A bridge cover entirely covering the plurality of subpatterns may be prepared on the top surface of the fluid flow part.

The microfluidic system for analyzing nucleic acid may further include a recess pattern on the bottom surface of the fluid flow part for forming one or more metering chambers for quantifying an amount of the lysis buffer supplied from the lysis buffer chamber of the reagent supply device. The microfluidic system for analyzing nucleic acid may further include on the bottom surface of the fluid flow part a recess pattern for forming one or more bubble trap chambers for removing bubbles generated in the binding-lysis chamber during cell lysis. A recess pattern for forming a plurality of metering chambers for quantifying an amount of the cell lysate formed in the binding-lysis chamber and for distributing the cell lysate into the plurality of rehydration chambers may be formed on the bottom surface of the fluid flow part.

A guide part for installing the reagent supply device may be further disposed on an upper portion of the fluid flow part.

The fluid flow part may be formed of a transparent polymer material, such as, for example, any one of polycarbonate ("PC"), polymethyl methacrylate ("PMMA"), polystyrene ("PS"), cyclic olefin copolymer ("COC"), polydimethylsiloxane ("PDMS"), and silicone.

The membrane part may be formed of PDMS or silicone.

The pneumatic part may be formed of a transparent polymer material.

BRIEF DESCRIPTION OF THE DRAWINGS

These and/or other aspects will become apparent and more readily appreciated from the following description of the embodiments taken in conjunction with the accompanying drawings, of which.

DETAILED DESCRIPTION

Figure 1:
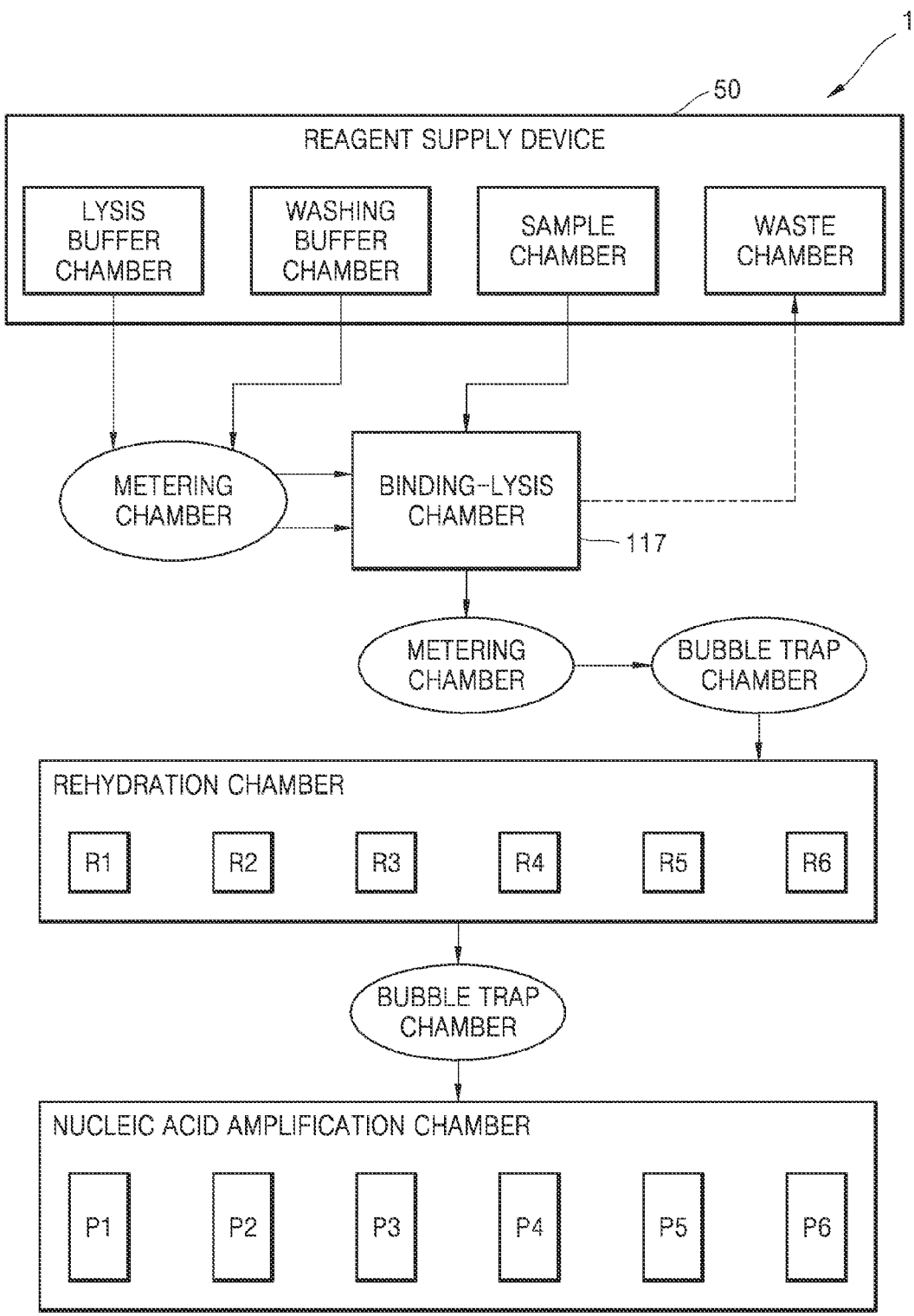
FIG. 1 is a block diagram illustrating a schematic structure of a microfluidic system.

Hereinafter, the present invention will be described in detail according to exemplary embodiments. Like reference numerals in the drawings denote like elements, and the size of each element in the drawings may be exaggerated for convenience of description and clarity. As used herein, the term "and/or" includes any and all combinations of one or more of the associated listed items.

Figure 2:
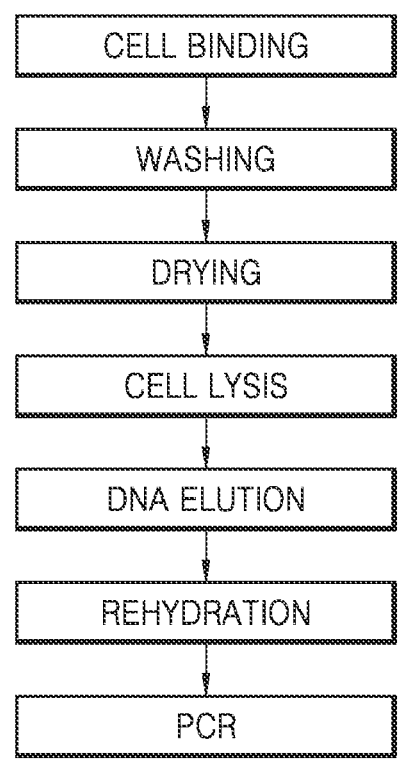
FIG. 2 is a flowchart illustrating a series of processes performed in the microfluidic system.

FIG. 1 is a block diagram illustrating a schematic structure of a microfluidic system 1 according to an embodiment of the present invention, and FIG. 2 is a flowchart illustrating a series of processes performed in the microfluidic system 1 according to an embodiment of the present invention.

The microfluidic system includes a reagent supply device 50, a binding-lysis chamber 117, rehydration chambers R1 to R6, nucleic acid amplification chambers P1 to P6, and a flow channel system (not shown) forming an integrated fluid flow between the reagent supply device 50, the binding-lysis chamber 117, the rehydration chambers R1 to R6, and the nucleic acid amplification chambers P1 to P6.

The reagent supply device 50 is a device able to store, transfer, and supply a sample as an examination target and a reaction reagent used for examining the sample, and includes a sample chamber in which the sample is injected, a plurality of reagent chambers, and a waste chamber in which the used reagent is discarded. The plurality of reagent chambers, for example, may be a lysis buffer chamber in which a lysis buffer for cell lysis is injected, and a washing buffer chamber in which a washing buffer is injected.

A series of processes, such as cell binding and DNA elution, is conducted in binding-lysis chamber 117. A plurality of particles for cell binding is disposed in the binding-lysis chamber 117. A diameter of each particle may be in a range of about 1 μm to about 1000 μm and an amount of each particle may be in a range of about 1 mg to about 100 mg. Each particle may have a random shape. Each particle may have a shape such as a bead, a sphere, a flat plate, a pillar, a sieve or filter, a gel, a layer, a fiber, or a combination thereof. Also, the particles may have magnetic properties. The particles may be formed, for example, of glass, silica, latex, or a polymeric material.

When the sample is injected into the binding-lysis chamber 117 from the sample chamber, cells are combined with the plurality of particles prepared in the binding-lysis chamber 117. Surfaces of the particles may include a material combined with the cell and the material may be specifically or nonspecifically combined with the cell. The material may include a substance, for example an antibody or a ligand, specifically combined with a substance on a surface of the cell. The material may be a hydrophobic material having a water contact angle ranging from about 70 degrees to about 90 degrees or a material having one or more amino groups. Examples of the hydrophobic material may be materials having a surface formed of octadecyltrichlorosilane ("OTS"), tridecafluorotetrahydrooctyl trimethoxysilane ("DTS"), octadecyldimethyl(3-trimethoxysilyl propyl)ammonium chloride ("OTC"), and polyethyleneiminetrimethoxysilane ("PEIM").

Next, a washing buffer is injected from the washing buffer chamber into the binding-lysis chamber 117 to wash the particles with the captured cells using a method of washing various debris or a buffer used during cell binding, and the particles may be dried by the injection of a gas such as air.

Thereafter, a lysis-buffer is injected from the lysis buffer chamber into the binding-lysis chamber 117, and external vibration is applied to the binding-lysis chamber 117 to vibrate the particles, lysing the cells so that nucleic acid may flow out of the binding-lysis chamber 117. A cell lysate formed in the binding-lysis chamber 117 and a nucleic acid amplification reagent, for example, a PCR reagent, are mixed in rehydration chambers R1 to R6. The plurality of rehydration chambers R1 to R6 is included for a multiplex PCR, but the present invention is not limited to the illustrated number of rehydration chambers. The cell lysate formed in the binding-lysis chamber 117 is distributed and introduced into each of the plurality of rehydration chambers R1 to R6. The nucleic acid amplification reagent may include, for example, a probe, a primer, an enzyme, or a combination thereof, and also may be disposed in a freeze-dried form in the rehydration chambers R1 to R6. The enzyme may include a polymerase. Rehydration chambers R1 to R6 may have a shape in which the freeze-dried nucleic acid amplification reagent and the cell lysate mix well with each other, and the mixture may then be extracted from rehydration chambers R1 to R6. The detailed shape of rehydration chambers R1 to R6 will further described below.

The nucleic acid amplification chambers may, for example, be a plurality of PCR chambers P1 to P6 and may correspond to the plurality of rehydration chambers R1 to R6. In each of the plurality of PCR chambers P1 to P6, a nucleic acid amplification reaction is performed on an amplification reaction mixture, for example a PCR mixture, which is introduced into the plurality of rehydration chambers R1 to R6.

Hereinafter, a PCR will be exemplified as a nucleic acid amplification reaction performed in the microfluidic system 1 and will be described by using expressions such as PCR chamber, PCR reagent, and PCR mixture. However, these expressions are described as examples of, respectively, an amplification chamber, a nucleic acid amplification reagent, and an amplification reaction mixture. In addition to the PCR, various other types of nucleic acid amplification reactions may be performed in the microfluidic system 1.

The microfluidic system 1 may include one or more metering chambers for quantifying an amount of a buffer supplied from the reagent supply device 50 to the binding-lysis chamber 117, and may also include one or more bubble trap chambers for removing bubbles which may be produced during a process of cell lysis. The metering chambers may be disposed in a flow channel from the reagent supply device 50 toward the binding-lysis chamber 117 and in a flow channel from the binding-lysis chamber 117 toward rehydration chambers R1 to R6. The bubble trap chambers may be disposed in the flow channel from the binding-lysis chamber 117 toward rehydration chambers R1 to R6 and/or in flow channels from rehydration chambers R1 to R6 toward PCR chambers P1 to P6.

Hereinafter, a detailed configuration of the microfluidic system 1 implementing the integrated flow channel system between the reagent supply device 50 and the plurality of chambers will be described.

Figure 3:
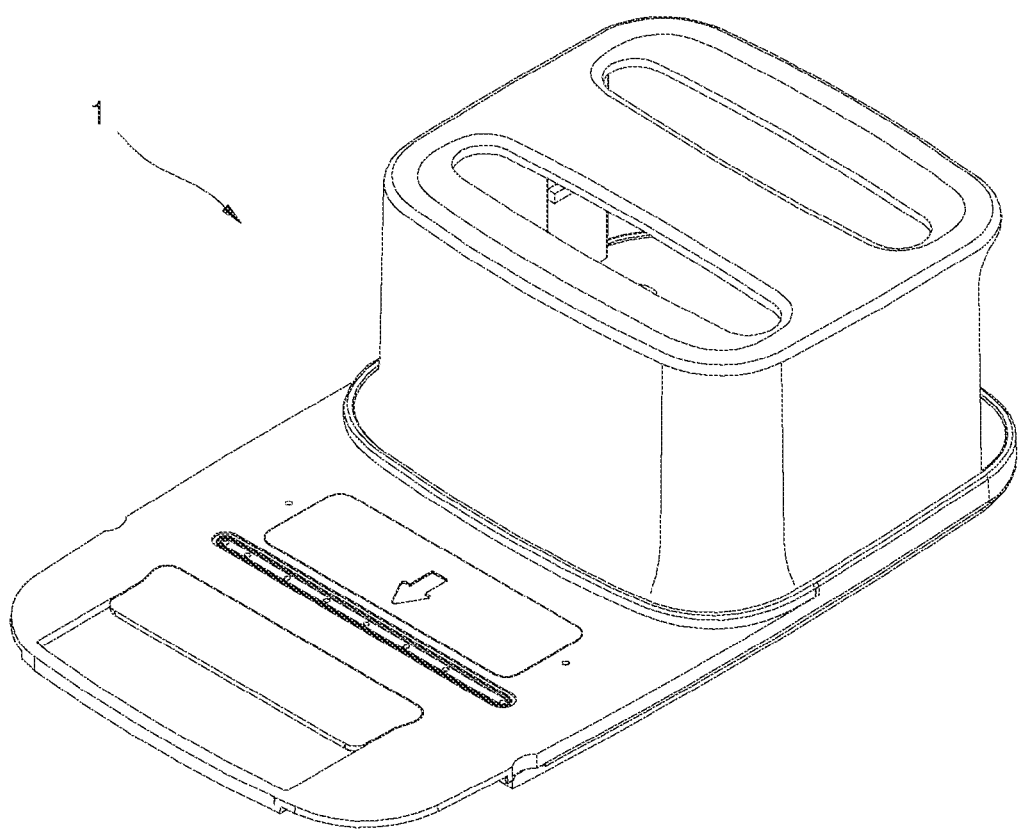
FIG. 3 is a perspective view illustrating a schematic external appearance of the microfluidic system.
Figure 4:
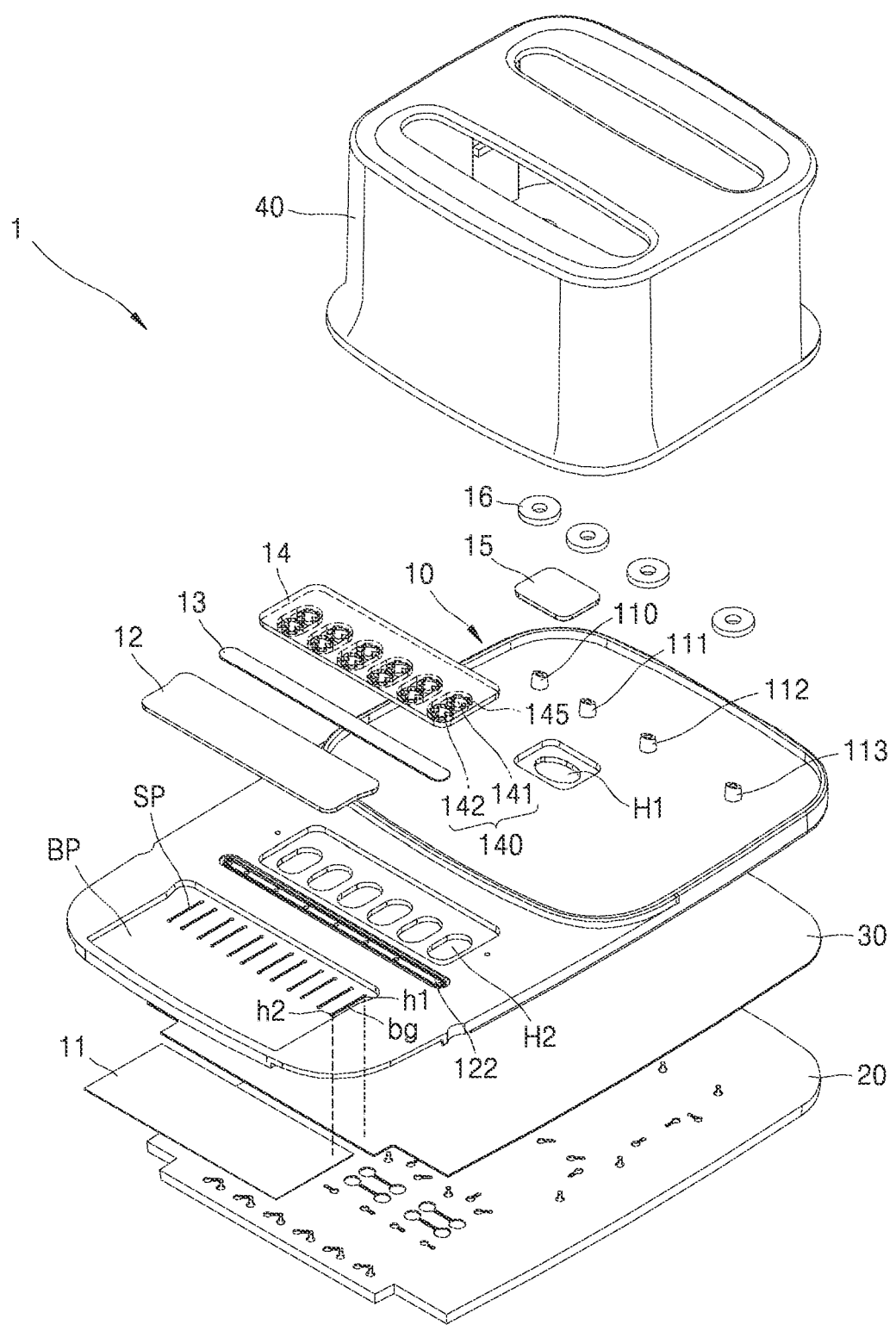
FIG. 4 is an exploded perspective view illustrating components constituting the microfluidic system of FIG. 3.

FIG. 3 is a perspective view illustrating a schematic external appearance of the microfluidic system 1 according to an embodiment of the present invention, and FIG. 4 is an exploded perspective view illustrating components constituting the microfluidic system 1 of FIG. 3.

The microfluidic system 1 broadly includes a fluid flow part 10, a pneumatic part 20, and a membrane part 30, and may further include a guide part 40 for installation of the reagent supply device (not shown).

Figure 7:
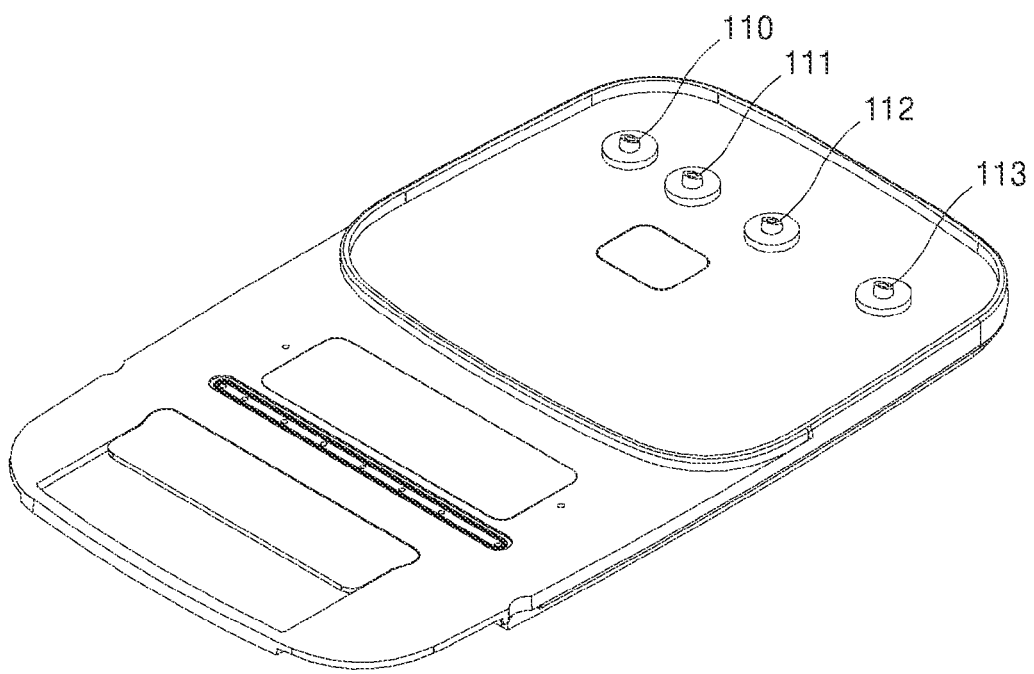
FIG. 7 illustrates needle-type inlets and an outlet formed on a top surface of the fluid flow part of the microfluidic system in FIG. 3.

As shown in FIG. 4, the fluid flow part 10 includes patterns, such as various through holes and inlets, constituting various channels, valves, and chambers that control the flow of a fluid to be examined. Fluid flow part 10 is formed of a transparent plastic material. For example, fluid flow part 10 may be formed of any one of polycarbonate ("PC"), polymethyl methacrylate ("PMMA"), polystyrene ("PS"), cyclic olefin copolymer ("COC"), polydimethylsiloxane ("PDMS"), and silicon, as a transparent polymer. Fluid flow part 10 includes inlets 110, 111, and 112 and outlet 113 connected to reagent supply device 50. Inlets 110, 111, and 112 and outlet 113 may be needle-shaped so as to allow a reagent to be released from reagent supply device 50 by breaking or rupturing a bottom surface of reagent supply device 50. FIG. 7 illustrates the needle-type inlets 110, 111, 112 and outlet 113 in detail. Fluid flow part 10 may also include a first through hole H1 forming a space defining, in part, the binding-lysis chamber 117 and a plurality of second through holes H2 forming spaces defining in part the plurality of rehydration chambers R1-R6. Also, a groove pattern (not shown) recessed so as to form spaces defining in part the plurality of PCR chambers P1-P6 may be included on a bottom surface of fluid flow part 10. Furthermore, a plurality of patterns (not shown) recessed so as to form microchannels implementing the flow channel system and a valve seat (not shown), and a protruding pattern for forming microvalves able to block the flows of the fluid passing the microchannels by pneumatic pressure applied from the pneumatic part 20, are formed on the bottom surface of fluid flow part 10.

Membrane part 30 is bonded to the bottom surface of fluid flow part 10 to form bottom surfaces of binding-lysis chamber 117, the plurality of rehydration chambers R1-R6, the metering chambers, the bubble trap chambers, and various other channels. Membrane part 30 is formed of an elastic material such as PDMS or silicone.

Pneumatic part 20 is for applying pneumatic pressure to fluid flow part 10 and is bonded to a bottom surface of membrane part 30. A plurality of ports for applying pneumatic pressure at a predetermined position of membrane part 30 are formed in pneumatic part 20. For example, pneumatic pressure applied from pneumatic part 20 may act to generate particle beating, such as bead beating, for a process of cell lysis in binding-lysis chamber 117 and to mix a PCR reagent and a cell lysate in rehydration chambers R1-R6. That is, membrane part 30 vibrates according to the pneumatic pressure applied from pneumatic part 20 and transfers vibration energy into binding-lysis chamber 117 or the rehydration chambers R1-R6. Also, pneumatic pressure applied from pneumatic part 20 may act to open and close the plurality of microvalves formed in fluid flow part 10. That is, membrane part 30 is in contact with the valve seat formed on the bottom surface of fluid flow part 10 to close the valves or is spaced apart from the valve seat to open the valves according to the pneumatic pressure applied by pneumatic part 20.

A plurality of particles (not shown) for cell binding is disposed in first through hole H1 formed in fluid flow part 10, and particle cover 15 covers first through hole H1.

Rehydration cover 14 covers the plurality of second through holes H2 formed in fluid flow part 10. Protrusions 145 are formed on rehydration cover 14 at positions corresponding to second through holes H2, grooves 140 that are recessed in a predetermined shape are formed on protrusions 145, and a PCR reagent (not shown) in a freeze-dried state is disposed in grooves 140.

The cell lysate requires various reagents to undergo a PCR. The various reagents may include a probe, a primer, an enzyme, or a combination thereof. Because these reagents may evaporate or activity of an enzyme may be degraded when the reagents are in a liquid phase, the reagents may be disposed in a freeze-dried state in rehydration cover 14. Grooves 140 formed in rehydration cover 14 respectively include two subgrooves 141 and 142 separated from each other. The PCR reagent may be divided and disposed in the two subgrooves 141 and 142. For example, in each of the plurality of grooves 140, a nucleic acid-containing sample, for example, a sample including one or more of a probe and a primer, may be disposed in one subgroove 141 and an enzyme may be disposed in the other subgroove 142.

A diameter of protrusion 145 of rehydration cover 14 may be formed to be slightly, e.g., about 10 µm, larger than a diameter of second through hole H2, in order to form a seal without using a separate adhesive. In the case where an adhesive is used, it is likely to cause problems with the freeze-dried reagent. Rehydration cover 14 may be formed of a elastic material, for example, silicon or rubber, for more reliable sealing.

A PCR film 11 is formed on a bottom surface of PCR chambers P1-P6. That is, PCR film 11 is prepared at a position which may cover the groove pattern (not shown) recessed so as to form the spaces defining, in part, of PCR chambers P1-P6 on the bottom surface of fluid flow part 10.

A bridge pattern BP is formed on the top surface of the fluid flow part 10. Bridge pattern BP has a shape recessed from a top surface of fluid flow part 10 and forms a path in which the PCR mixture formed in rehydration chambers R1-R6 moves to PCR chambers P1-P6. Bridge pattern BP constitutes a channel for guiding PCR mixture that may flow over the top surface of fluid flow part 10 when the PCR mixture formed in rehydration chambers R1-R6 moves to PCR chambers P1-P6. Bridge pattern BP includes a plurality of subpatterns SP. Each of the plurality of subpatterns SP includes a hole h1 penetrating fluid flow part 10 to face membrane part 30, a hole h2 penetrating fluid flow part 10 to face PCR film 11, and a bridge groove bg connecting two holes h1 and h2 and recessed from the top surface of fluid flow part 10. Hole h2, which will be further described below, forms an inlet hole toward PCR chambers P1-P6 or an outlet hole from PCR chambers P1-P6. Furthermore, bridge cover 12 covers the plurality of subpatterns SP and is disposed on the top surface of fluid flow part 10. Ultrasonic welding energy directors (not shown) for ultrasonic joining with fluid flow part 10 may be formed on bridge cover 12. Alternatively, ultrasonic welding energy directors may be formed on fluid flow part 10, for example, near holes h1 and h2 and recessed bridge groove bg.

Vent channel 122 and vent cover 13 covering vent channel 122 are disposed on the top surface of fluid flow part 10. Vent channel 122 may release excess fluid for storage in a predetermined space when the fluid continuously flows after filling a predetermined chamber, such as when the flow of the fluid is not accurately detected. Vent channel 122 as illustrated in FIG. 4 may comprise a region recessed in a predetermined shape and a plurality of vent holes formed therein.

A plurality of recessed patterns (not shown) for forming the metering chambers and bubble trap chambers may be formed on the bottom surface of fluid flow part 10. For example, the recessed patterns may form one or more metering chambers for quantifying the amount of the lysis buffer supplied from the lysis buffer chamber of reagent supply device 50, and one or more bubble trap chambers for removing bubbles, generated in the binding-lysis chamber during the cell lysis. The recessed patterns may also form the plurality of metering chambers for quantifying an amount of cell lysate formed in the binding-lysis chamber and distributing the cell lysate into the plurality of rehydration chambers R1-R6.

A process of forming an assembly as in FIG. 3 is described below. First, fluid flow part 10 is prepared and PCR film 11 is attached to the bottom surface of fluid flow part 10 using any suitable adhesion method, including ultrasonic welding, an adhesive, or tape. Bridge cover 12 and vent cover 13 are also attached to the top surface of fluid flow part 10 by any suitable adhesion method. The bottom surface of fluid flow part 10, i.e., the surface to be bonded to membrane part 30, is coated with $SiO_2$ to a thickness of about 3,000 Å.

Pneumatic part 20 is prepared and each surface of pneumatic part 20 and membrane part 30 to be bonded is plasma treated. Pneumatic part 20 and membrane part 30 are bonded to each other. A bonding surface of $SiO_2$-coated fluid flow part 10 and a bonding surface of pneumatic part 20 bonded to membrane part 30 are plasma treated, and $SiO_2$-coated fluid flow part 10 and pneumatic part 20 bonded to membrane part 30 are bonded to each other.

Particles are injected into first through hole H1, forming the binding-lysis chamber, and particle cover 15 is bonded to first through hole HI by any suitable adhesion method.

O-rings 16 are inserted over each of inlet 110, 111, and 112 and outlet 113, guide part 40 is aligned with a top portion of fluid flow part 10, and guide part 40 and fluid flow part 10 are then bonded by any suitable adhesion method.

Figure 12A:
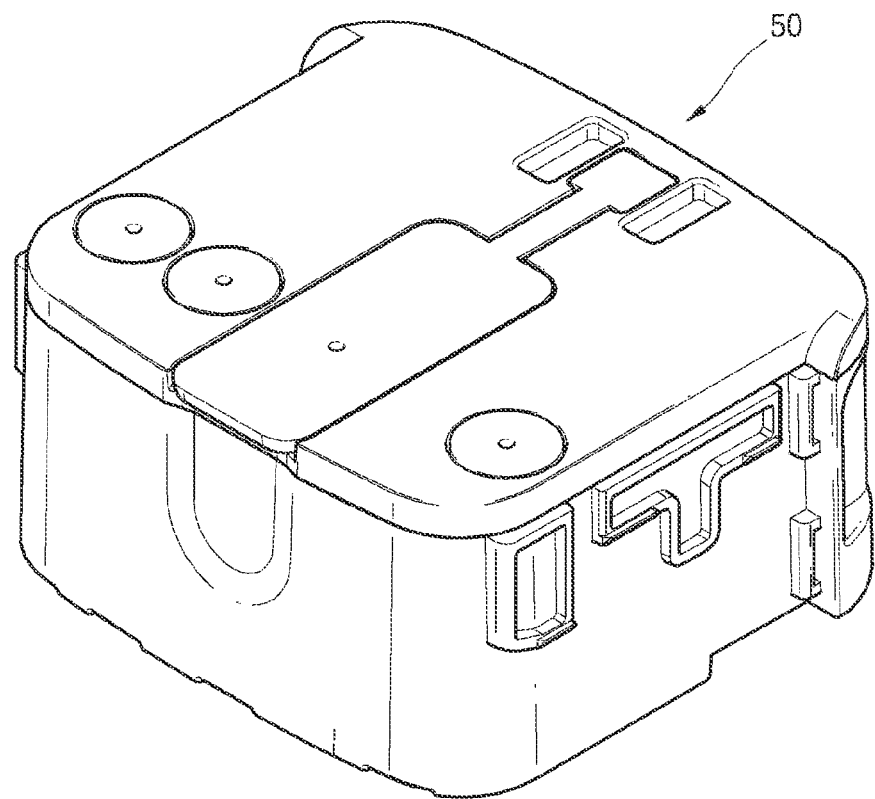
FIGS. 12A through 12C illustrate external structures of a reagent supply device.

Reagent supply device 50 (as shown in FIG. 12A) is installed by being inserted into guide part 40. O-rings 16 inserted between reagent supply device 50 and fluid flow part 10 may act to prevent leakage of a solution.

Rehydration cover 14, in which freeze-dried PCR reagent is disposed, is assembled on fluid flow part 10.

Figure 5:
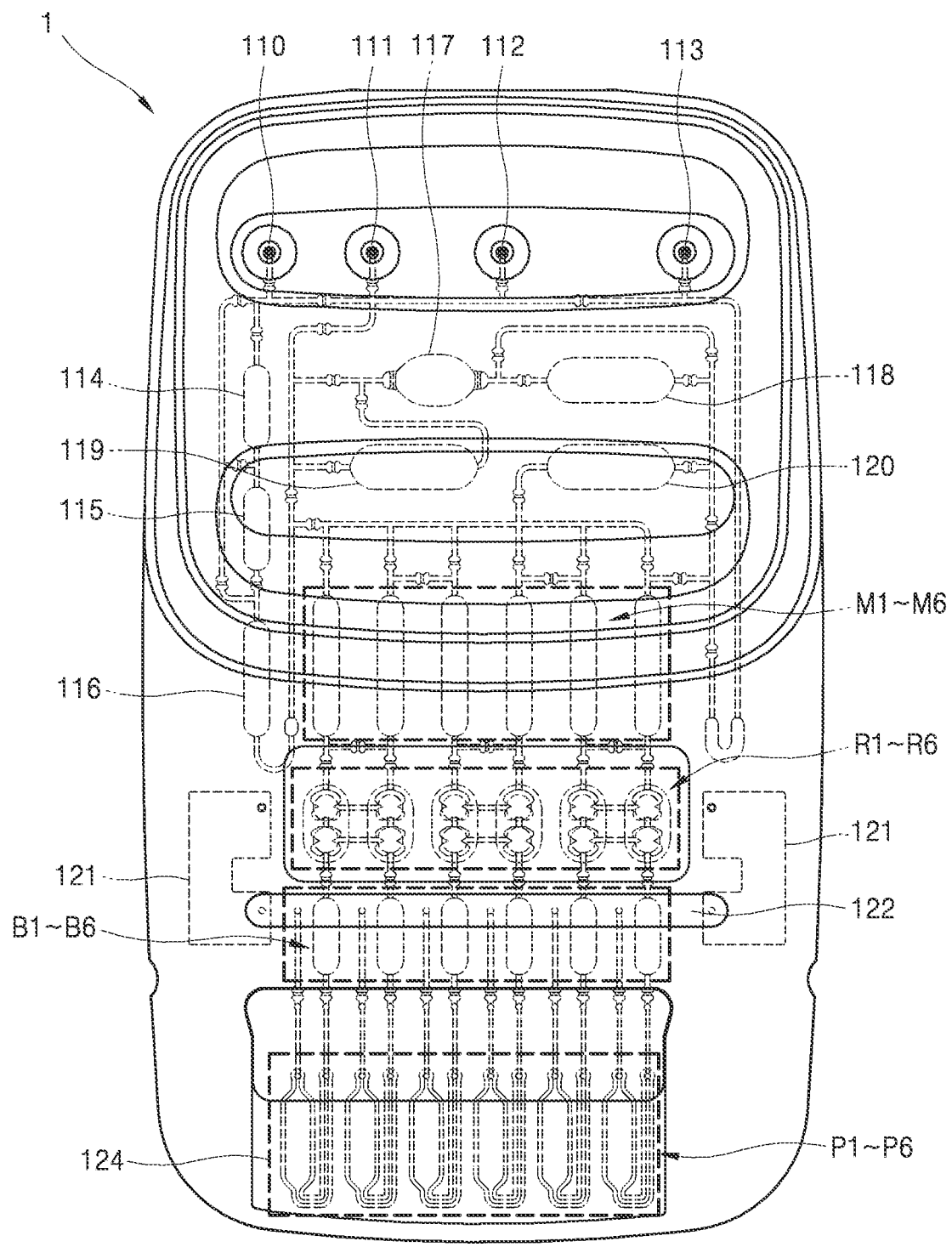
FIG. 5 is a plan view illustrating the microfluidic system of FIG. 3.

FIG. 5 is a plan view illustrating the microfluidic system 1 of FIG. 3. Reagents, including the lysis buffer, the washing buffer, and the sample, are respectively injected from reagent supply device 50 through a port which includes inlets 110, 111, and 112 and outlet 113. As illustrated in FIG. 4, because inlets 110, 111, and 112 and outlet 113 are tilted toward a direction of insertion when reagent supply device 50 is inserted from an opened direction of guide part 40, inlets 110, 111, and 112 and outlet 113 may be inserted into reagent supply device 50 when it slides over the needle shape of inlets 110, 111, and 112 and outlet 113. In this manner inlets 110, 111, and 112 and outlet 113 may act to prepare paths by penetrating a membrane constituting the bottom surface of reagent supply device 50 so as to allow the reagent stored therein to be released.

Metering chambers 114, 115, and 116 are for quantifying the lysis buffer introduced through inlet 110. For example, NaOH may be used as a lysis buffer for cell lysis and an enrichment effect may increase when the lysis buffer having a volume as small as possible is used and is transferred to PCR chambers P1-P6 without loss.

Metering chambers 114, 115, and 116 may have different volumes from one another. For example, metering chambers 114, 115, and 116 may have a volume of about 8 µl, about 8 µl, and about 12 µl, respectively. Because about 12 µl of the lysis buffer may be used when only metering chamber 116 is used, metering chamber 116, for example, may be used in the case where two of the six PCR chambers P1-P6 are used, each PCR chamber having a volume of about 4 µl. When metering chambers 115 and 116 are simultaneously used, about 20 µl of the lysis buffer may be used, and thus, four of the six PCR chambers P1-P6 may be used. When metering chambers 114, 115 and 116 are simultaneously used, about 28 µl of the lysis buffer may be used, and thus, all six PCR chambers P1-P6 may be used. About 4 µl of a dead volume may exist even in the case where any combination of metering chambers 114, 115, and 116 is used and thus, PCR chambers P1-P6 may be filled even in the case where some of the sample is lost. The number of metering chambers and the volume of each are exemplary and may be variously changed.

In a channel connected to binding-lysis chamber 117, a weir having a gap of about 20 µm may be formed from a bottom of the channel to a ceiling thereof in order for the particles injected into binding-lysis chamber 117 for cell binding not to be released.

In one embodiment, bubble trap chambers 118, 119, and 120 each have a volume of about 28 µl. Bubble trap chambers 118, 119, and 120 reciprocate the buffer in the case where cells having a low concentration are attempted to be analyzed, and also remove bubbles which may be generated after the cell lysis through the movement of membrane part 30. That is, bubble trap chambers 118, 119, and 120 reciprocate an elution buffer in a forward direction (bubble trap chamber 119→binding-lysis chamber 117→bubble trap chamber 118) and a backward direction (bubble trap chamber 118→binding-lysis chamber 117→bubble trap chamber 119) centered on binding-lysis chamber 117. A buffer that is the same as the lysis buffer may be used as the elution buffer and the buffer may be used as the elution buffer by being further added after the lysis. In one embodiment, bubble trap chambers 118, 119, and 120 may have a volume which may entirely accommodate a maximum volume of about 28 µl during the reciprocation of the buffer. Bubble trap chamber 120 removes bubbles of the cell lysate being subjected to an entire DNA elution process to prevent various errors due to the bubbles during a subsequent process. The number of bubble trap chambers and the volume of each are exemplary and may be variously changed.

Two confining chambers 121 positioned at both sides of vent channel 122 act to confine the fluid containing the reagent and the sample so as not to flow out through vent channel 122 due to potential system errors. That is, when PCR chambers P1-P6 are accurately filled and the flow of the fluid is accurately stopped by being detected by the system, the fluid does not flow out through vent channel 122. However, when the flow of the fluid is not detected after PCR chambers P1-P6 are filled with the fluid and the fluid continuously flows, the fluid may flow out through vent channel 122 to be collected in confining chambers 121 at both sides thereof.

Domain 124, as a top portion of PCR chambers P1-P6, is an optical window for observing changes in an amount of fluorescence according to the process of the PCR. Domain 124 is prepared to be thinner than the surrounding are so as to allow as small amount of fluorescence as possible to be transmitted out. Metering chambers M1-M6, in one embodiment each having a volume of about 4 µl, may distribute and store the lysate passing through bubble trap chamber 120 in amounts of about 4 µl, respectively. The cell lysate stored in the metering chambers M1-M6 is respectively injected into rehydration chambers R1-R6 and mixed with the probe, the primer, the enzyme, or a combination thereof, is freeze-dried, and stored in rehydration chambers R1-R6 by the movement of membrane part 30 to prepare a PCR mixture.

A PCR, the last operation of an analysis process using the microfluidic system 1, is performed in PCR chambers P1-P6. The PCR mixture passing through rehydration chambers R1-R6 passes through bubble trap chambers B1-B6, and is then injected into PCR chambers P1-P6. Because, in one embodiment, about 4 µl of the PCR mixture is used to fill an entire region of the channels connected to PCR chambers P1-P6 without bubbles as well as PCR chambers P1-P6, a volume actually participating in the PCR may be about 2.5 µl.

Figure 6A:
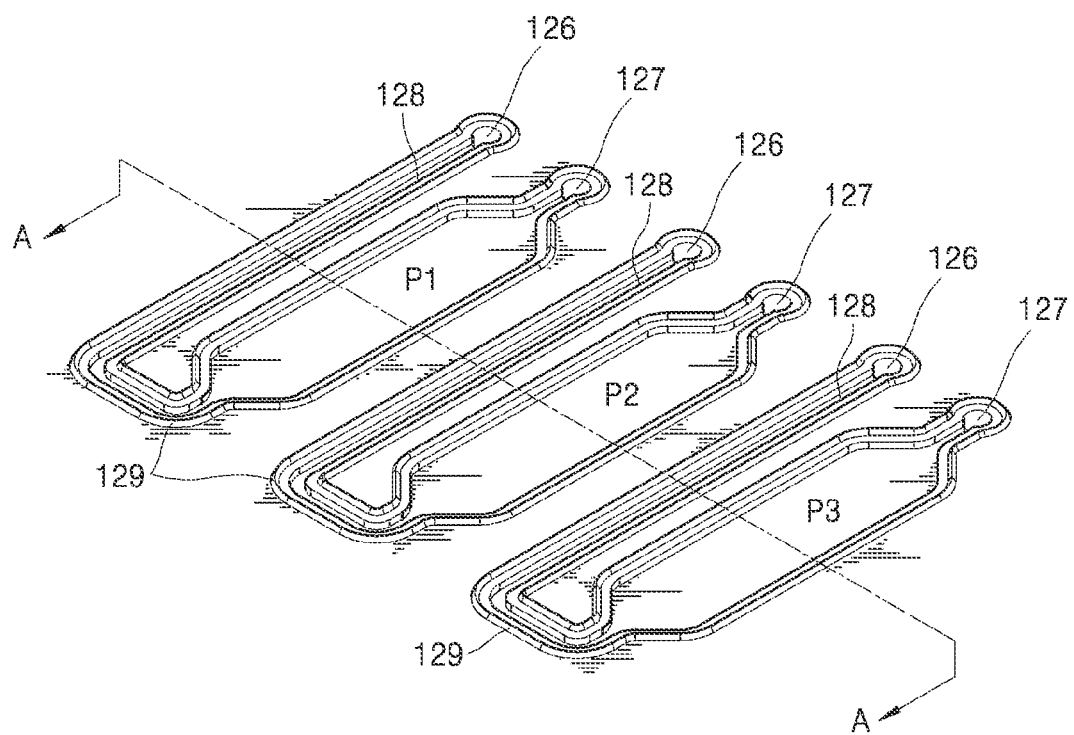
FIG. 6A illustrates groove patterns for forming spaces of PCR chambers formed on a bottom surface of a fluid flow part of the microfluidic system in FIG. 3.
Figure 6B:
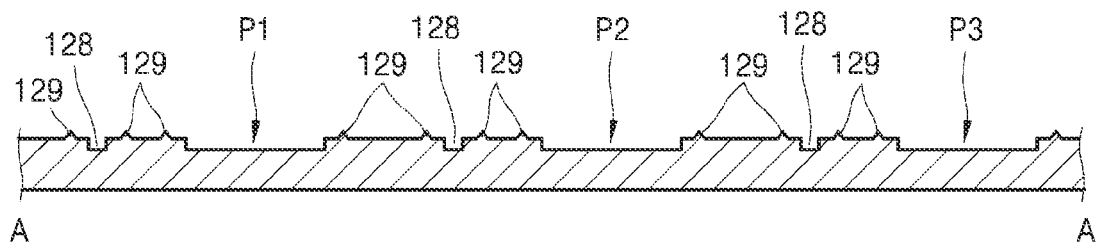
FIG. 6B is a cross-sectional view taken along line A-A in FIG. 6A.

FIG. 6A illustrates groove patterns for forming spaces of PCR chamber P1-P6 formed on the bottom surface of fluid flow part 10 of FIG. 4, and FIG. 6B is a cross-sectional view taken along line A-A in FIG. 6A. For convenience, FIGS. 6A and 6B exemplarily illustrate only three PCR chambers P1-P3. The other three PCR chambers P4-P6 have the same structure.

An inlet hole 126, an inlet channel 128, and an outlet hole 127 are connected to each of PCR chambers P1-P6. The PCR mixture introduced through inlet hole 126 flows in along inlet channel 128 to fill each PCR chamber P1-P6 and then flows out of each PCR chamber P1-P6 through outlet hole 127. Inlet hole 126 and outlet hole 127 are not disposed on opposite sides with respect to PCR chambers P1-P6, but are disposed on the same side for the miniaturization of the microfluidic system 1 and the maximization of a fluorescence signal. Thus, since depths of PCR chambers P1-P6 are secured in a predetermined range, a higher fluorescence signal may be obtained and a deviation in temperatures between PCR chambers P1-P6 may be reduced by arranging the six PCR chambers P1-P6 as close to one another as possible. PCR film 11 is attached to the bottom surface of fluid flow part 10 in order to form bottom surfaces of PCR chambers P1-P6 and effectively transfer heat. Ultrasonic welding or any suitable adhesion method may be used to attach PCR film 11 to the bottom surface of fluid flow part 10. Energy directors 129 having a height of about 100 μm may be formed for the ultrasonic welding. As illustrated in FIG. 6B, energy directors 129 may be formed at a predetermined interval from inlet channel 128 and corners of PCR chambers P1-P6.

Figure 8A:
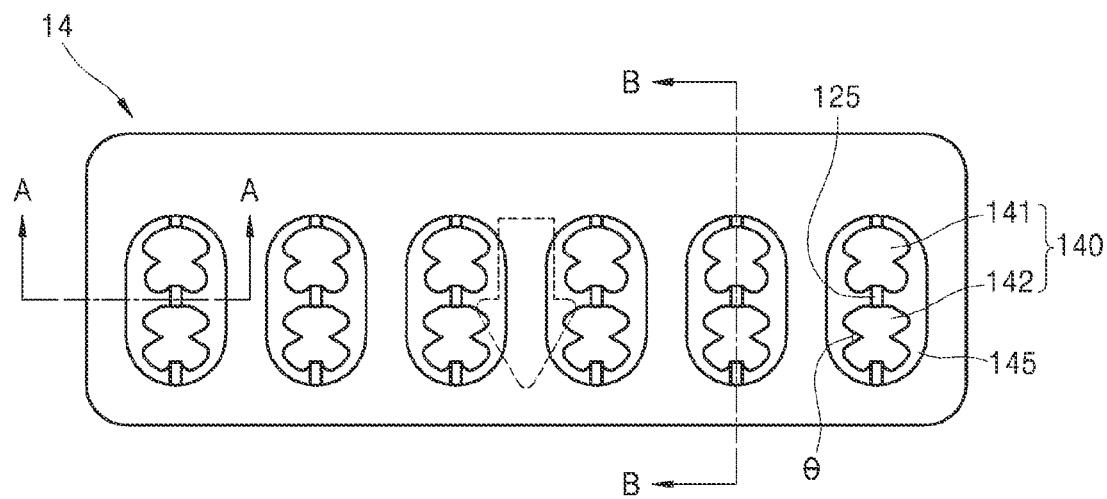
FIG. 8A is a plan view illustrating a structure of a rehydration cover.
Figure 8B:
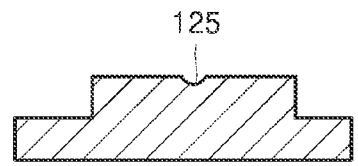
FIG. 8B is a cross-sectional view taken along line A-A in FIG. 8A.
Figure 8C:
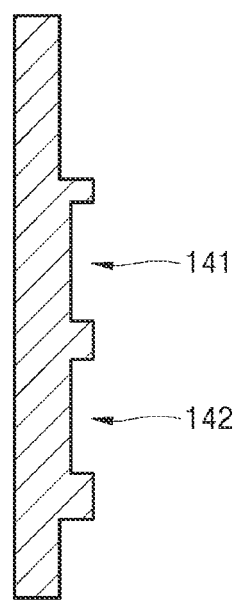
FIG. 8C is a cross-sectional view taken along line B-B in FIG. 8A.

FIG. 8A is a plan view illustrating a structure of rehydration cover 14, FIG. 8B is a cross-sectional view taken along line A-A in FIG. 8A, and FIG. 8C is a cross-sectional view taken along line B-B in FIG. 8A.

Rehydration cover 14 is for forming the six rehydration chambers R1-R6 and includes six protrusions 145 corresponding to six through holes forming the spaces of rehydration chambers R1-R6. Recessed groove 140 is formed in each protrusion 145 and each groove includes the two subgrooves 141 and 142. A sample including a probe, a primer, or a combination thereof is freeze-dried and contained in subgroove 141, and a sample including an enzyme is freeze-dried and contained in subgroove 142. An arrow represents a direction of the movement of the fluid. Subgrooves 141 and 142 are connected through microchannel 125. The cell lysate is introduced from an upper side of subgroove 141 to fill subgroove 141 and then passes through microchannel 125 to fill subgroove 142. A shape of subgrooves 141 and 142 is formed so as to allow the cell lysate to be easily released without leaving a residue in subgrooves 141 and 142 after the cell lysate fills subgrooves 141 and 142 without bubbles and is mixed with the PCR reagents by the movement of membrane part 30. The shape of subgrooves 141 and 142 may be determined through hydrodynamic analysis in consideration of surface properties of the inner surfaces of subgrooves 141 and 142 and solution properties of the nucleic acid lysate. As illustrated in FIG. 8A, sides of subgrooves 141 and 142 may have a curved shape and a width of a center portion thereof may be the smallest width of the subgroove. An external angle θ formed by corners of the narrow center of subgrooves 141 and 142 may be in a range of about 30 degrees to about 90 degrees.

Figure 9A:
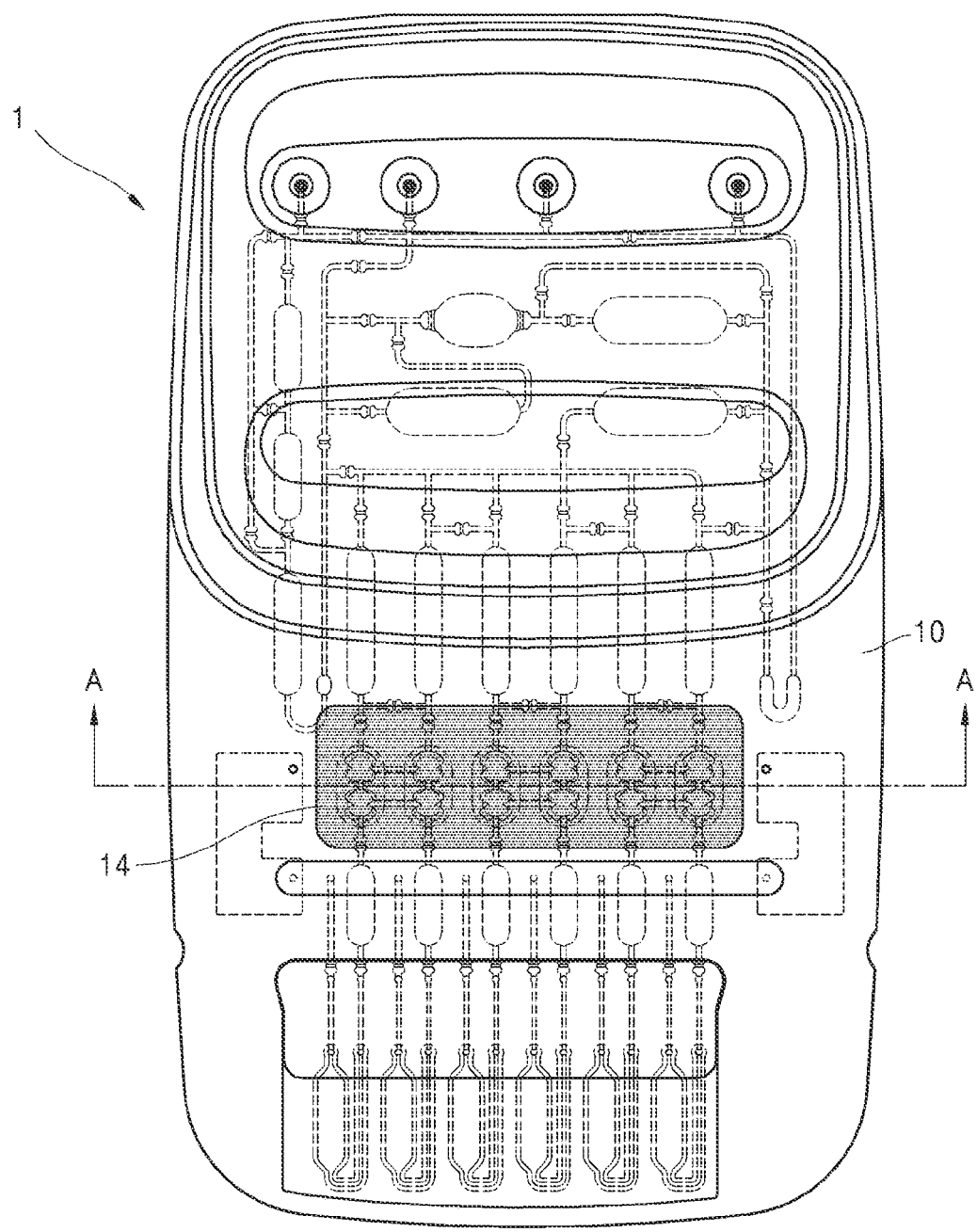
FIG. 9A is a plan view illustrating a state in which a rehydration cover and a fluid flow part are combined.
Figure 9B:
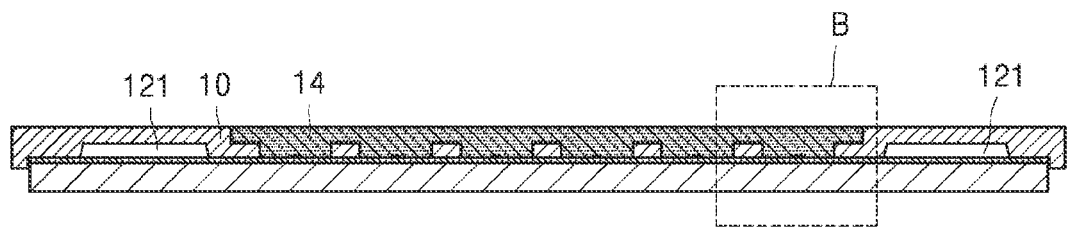
FIG. 9B is a cross-sectional view taken along line A-A in FIG. 9A.
Figure 9C:
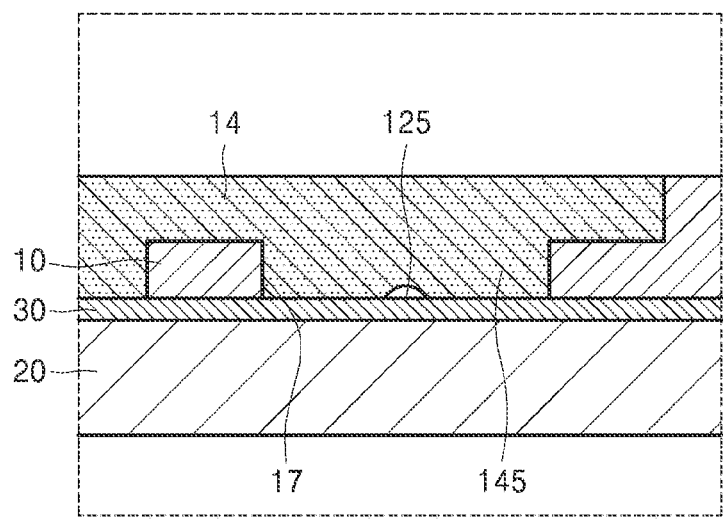
FIG. 9C is an enlarged view illustrating a detailed portion of FIG. 9B.

FIG. 9A is a plan view illustrating a state in which rehydration cover 14 and fluid flow part 10 are combined, FIG. 9B is a cross-sectional view taken along line A-A in FIG. 9A, and FIG. 9C is an enlarged view illustrating a detailed portion of FIG. 9B.

In one embodiment, a separate adhesive is not used during the combination of rehydration cover 14 and fluid flow part 10, but properties of materials constituting each component are used to form a seal. An adhesive may cause problems with the freeze-dried PCR reagents. As described above, the seal may be formed by forming the diameter of protrusion 145 of rehydration cover 14 to be slightly larger than the diameter of second through hole H2 in which protrusion 145 is inserted in fluid flow part 10. In this case, the protrusion may be provided by a deformable (e.g., elastic) material. FIG. 9C illustrates a position of microchannel 125 connecting subgrooves 141 and 142 after the completion of the combination, and when the combination is accurately completed as above, a leakage along an interface 17 between fluid flow part 10 and rehydration cover 14 may not occur and the solution may only move along microchannel 125.

Figure 10A:
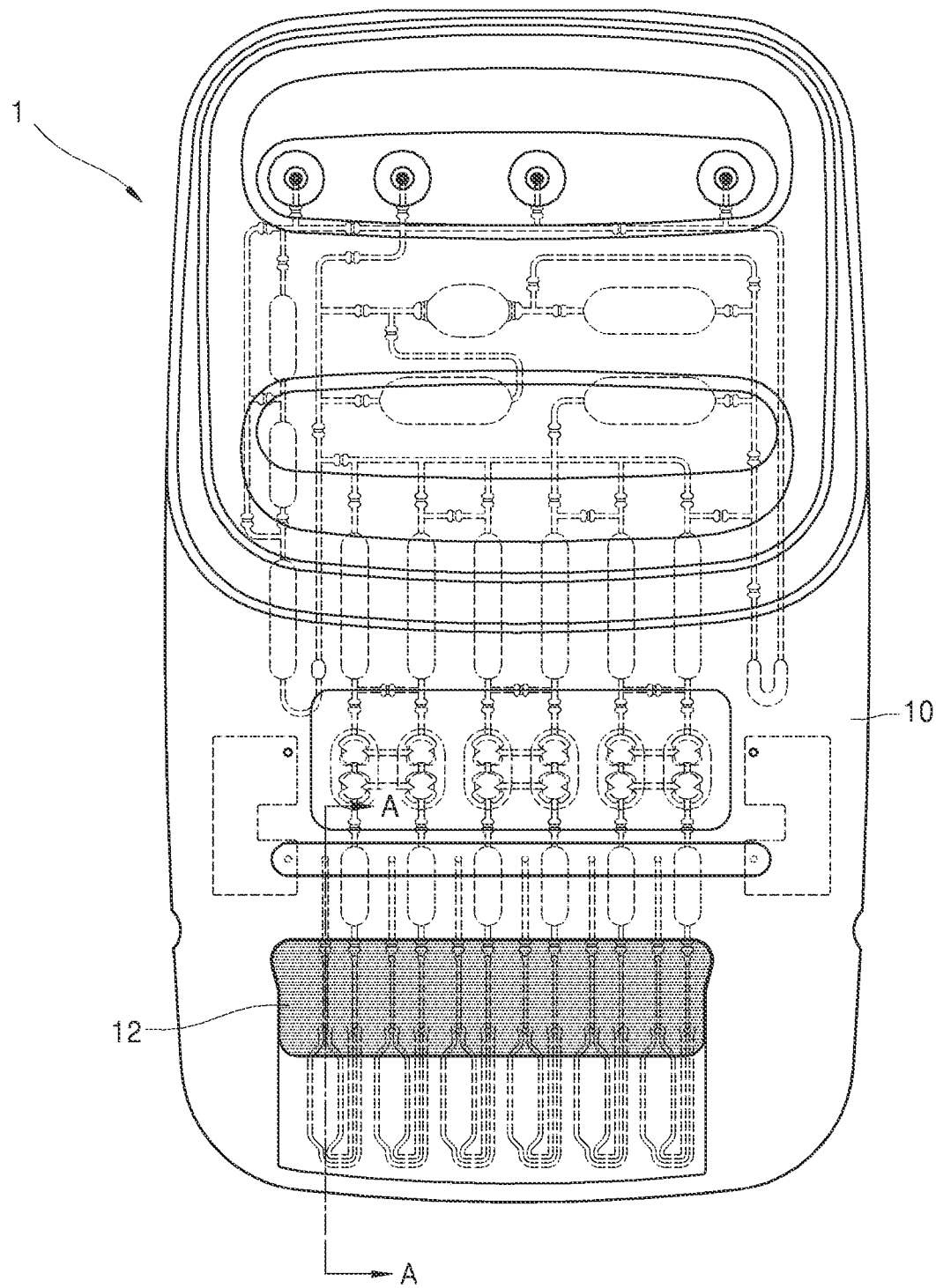
FIG. 10A is a plan view illustrating a state in which a bridge cover and a fluid flow part are combined.
Figure 10B:
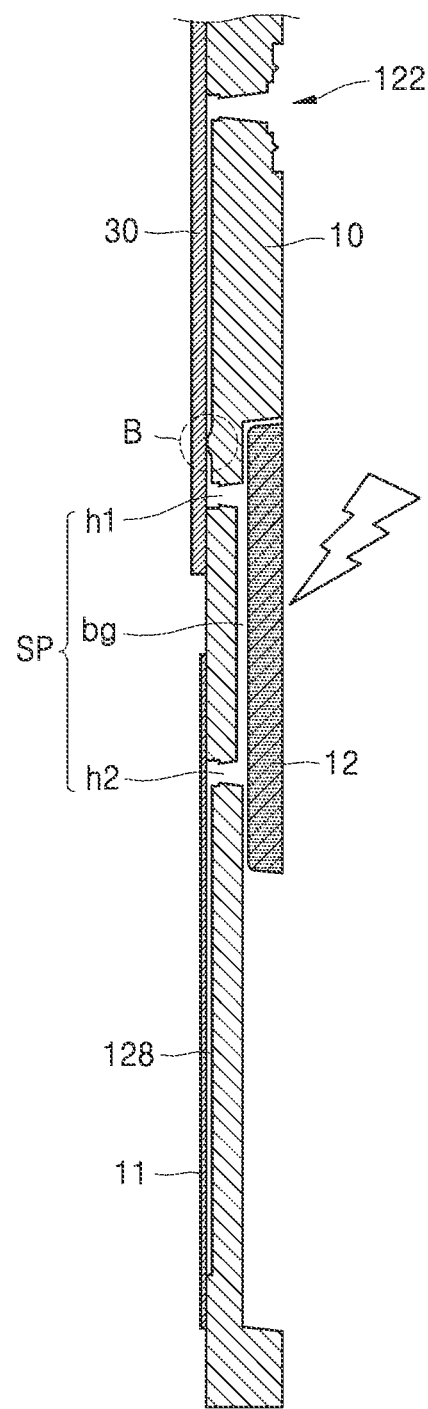
FIG. 10B is a cross-sectional view taken along line A-A in FIG. 10A.
Figure 10C:
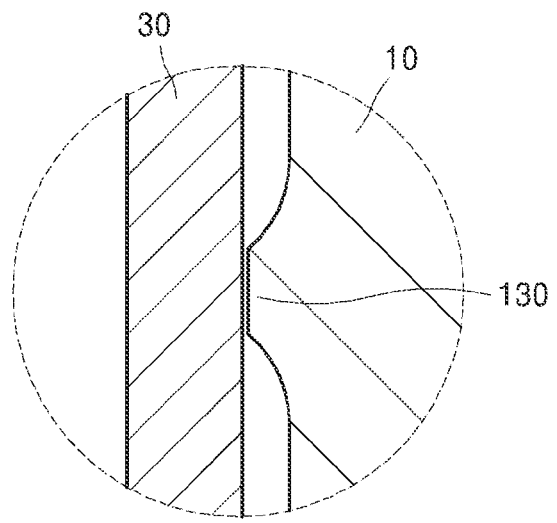
FIG. 10C is an enlarged view illustrating a detailed portion of FIG. 10B.

FIG. 10A is a plan view illustrating a state in which bridge cover 12 and fluid flow part 10 are combined, FIG. 10B is a cross-sectional view taken along line A-A in FIG. 10A, and FIG. 10C is an enlarged view illustrating a detailed portion of FIG. 10B.

Bridge cover 12 together with bridge pattern BP formed on the top surface of fluid flow part 10 enables the vertical movement of the fluid. Bridge pattern BP includes the plurality of subpatterns SP, and each subpattern SP includes hole h1 penetrating fluid flow part 10 to face membrane part 30, hole h2 penetrating fluid flow part 10 to face PCR film 11, and recessed bridge groove bg connecting two holes h1 and h2. In the cross section of FIG. 10B, hole h2 becomes the inlet hole (see 126 in FIG. 6A) connected to inlet channel 128 toward PCR chambers P1-P6. Because membrane part 30 is attached to the bottom surface of fluid flow part 10 and the bottom surfaces of PCR chambers P1-P6 are formed of PCR film 11, a channel connected to membrane part 30 and PCR film 11 may be difficult to form. For the flow of the fluid toward the PCR chambers P1-P6, the fluid passing through bubble trap chambers B1-B6 of fluid flow part 10 moves above fluid flow part 10 through hole h1 and flows into inlet channel 128 toward PCR chambers P1-P6 through hole h2 while moving along bridge groove bg. Bridge cover 12 may be welded to the top portion of fluid flow part 10 forming bridge pattern BP through ultrasonic welding. Through the bridge cover 12, fluid flow between holes h1 and h2 may be observed.

Bridge groove bg also acts as a channel for detecting the flow of the solution which fills PCR chambers P1-P6 and flows out therefrom. That is, when the flow of the solution is detected in bridge groove bg, the further introduction of the PCR mixture into PCR chambers P1-P6 is stopped.

FIG. 10C illustrates portion B of FIG. 10B in detail. The starting and stopping of the flow of the fluid is controlled according to the attachment or detachment of membrane part 30 to valve seat 130. Valve seat 130 is detached from membrane part 30 when no external pressure is applied to membrane part 30. That is, a microvalve is in a state of being opened. Such a configuration embodies a normally-open type valve, and is different from a normally-closed type in which membrane part 30 and valve seat 130 are in contact with each other when no external pressure is applied to membrane part 30. With respect to the normally-closed type valve, membrane part 30 may be naturally fixed to valve seat 130 due to a chemical or physical reaction when the microvalve does not operate for a prolonged period of time. Therefore, when the microvalve is not used for a prolonged period of time, an initialization for detaching membrane part 30 from valve seat 130 may be necessary. In the present exemplary embodiment, the microvalve is more easily realized by using a normally-open type valve.

When filling PCR chambers P1-P6, the valve in portion B is opened. That is, membrane part 30 is not allowed to be in contact with valve seat 130 to form an exhaust path toward vent channel 122, and when the flow of the solution in bridge groove bg under bridge cover 12 is detected to stop the introduction of the PCR mixture, the valve in portion B is closed.

Figure 11A:
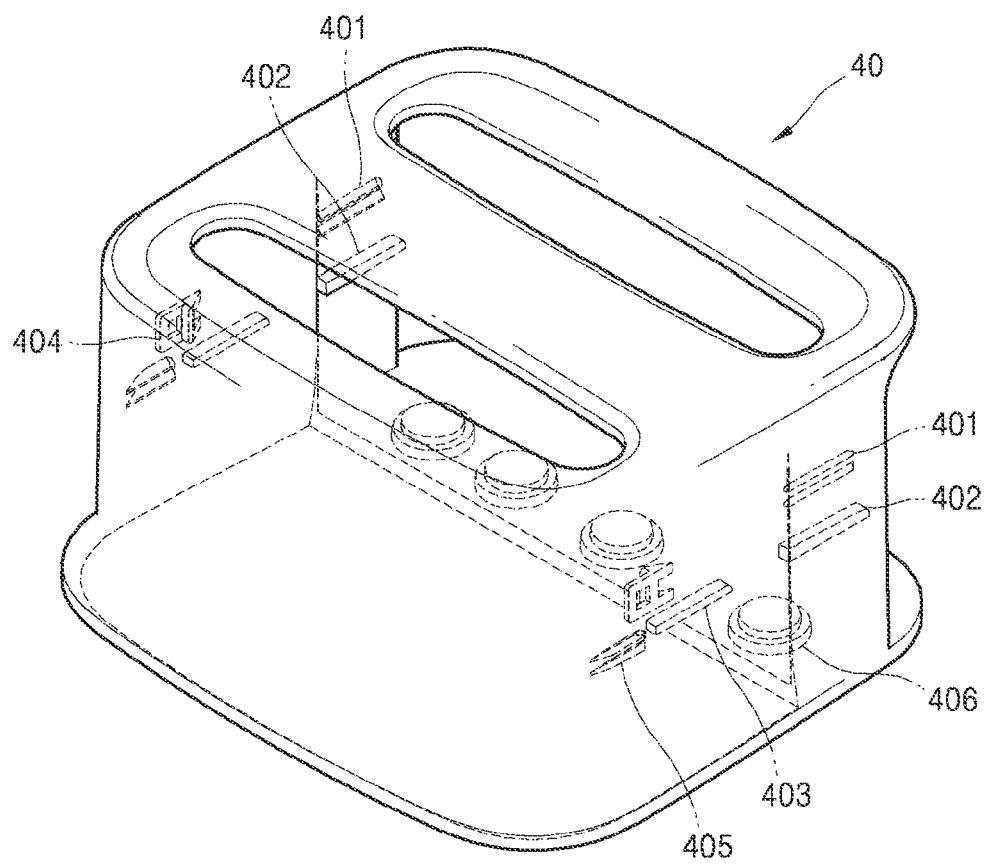
FIGS. 11A through 11C illustrate detailed structures of a guide part in which a reagent supply device is installed.
Figure 11B:
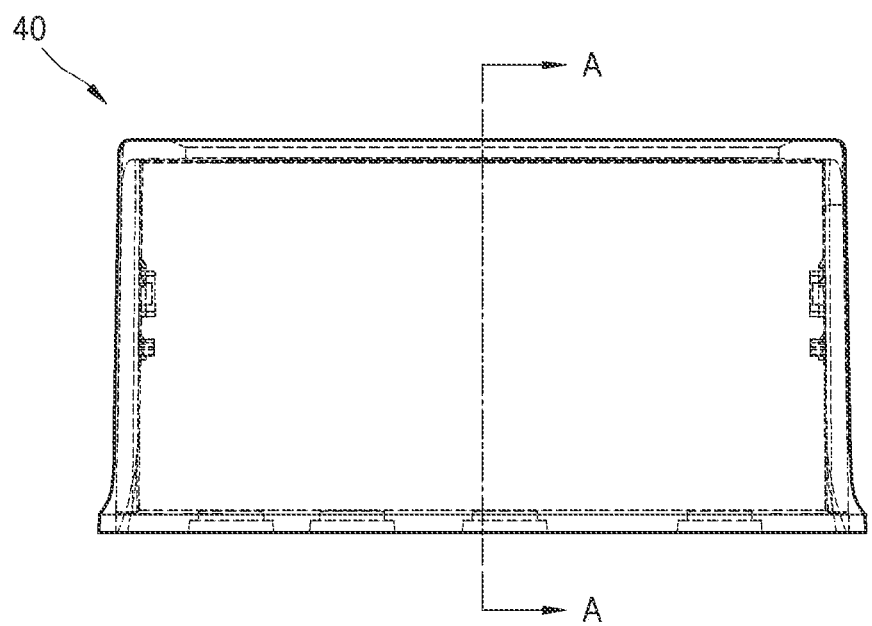
Figure 11C:
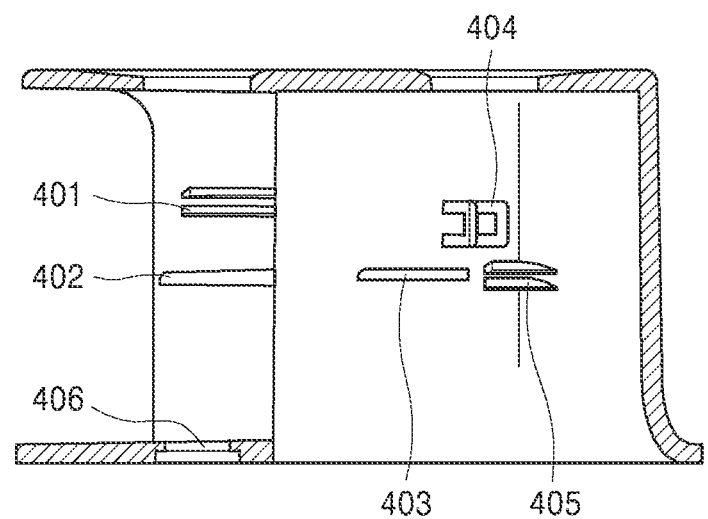
Figure 12B:
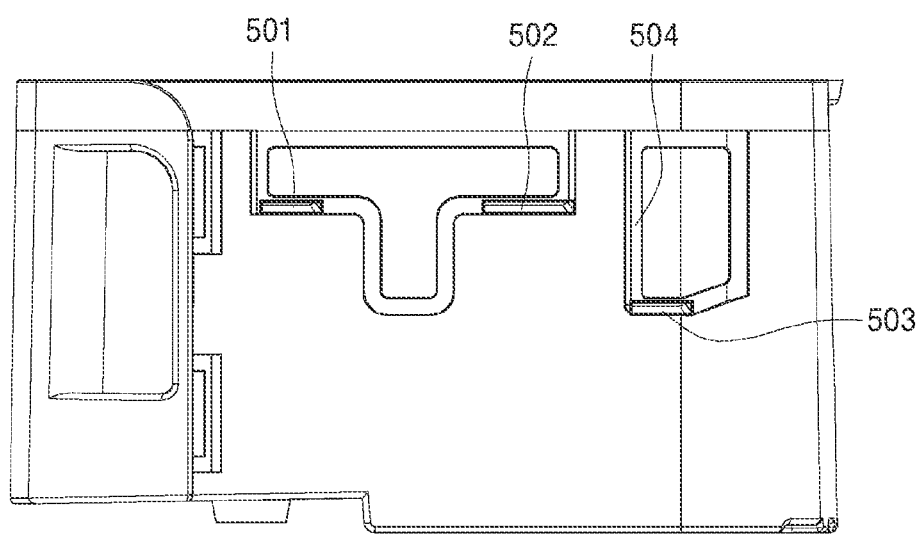
Figure 12C:
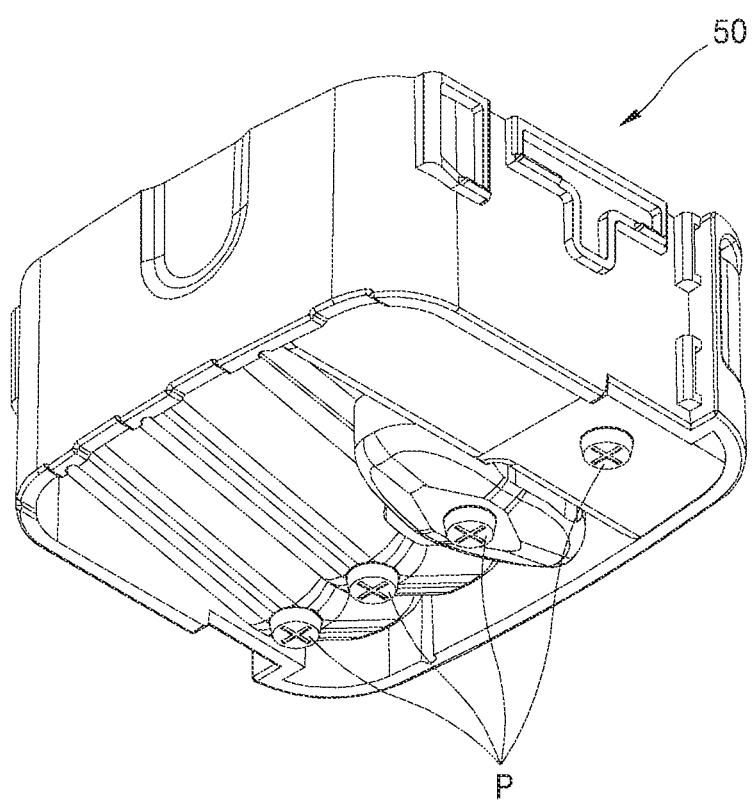

FIGS. 11A through 11C illustrate detailed structures of guide part 40 in which reagent supply device 50 is installed, and FIGS. 12A through 12C illustrate external structures of reagent supply device 50.

Horizontal axes of upper surfaces of structures 401 and 404 act as a support for sliding structures 501 and 502 thereon during insertion of reagent supply device 50, and for preventing damage in a case where membrane part 30 is punctured by being pressed downward. When reagent supply device 50 is accurately inserted up to a particular position, hooks disposed on a vertical axis of the structures 404 are fastened with the structures 504 to thus prevent reagent supply device 50 from being pushed backward again in an inserted direction. As illustrated in FIG. 12C, destruction patterns P are formed on the bottom surface of reagent supply device 50 and are broken by needle-shaped inlets 110, 111, and 112 and outlet 113 illustrated in FIG. 4 to allow the reagent and the sample to flow in and flow out of reagent supply device 50. In the operation in which destruction patterns P are being penetrated, structures 501, 502, and 503 are combined with structures 402, 403, and 405 to prevent the reagent supply device 50 from being raised upward.

Figure 13A:
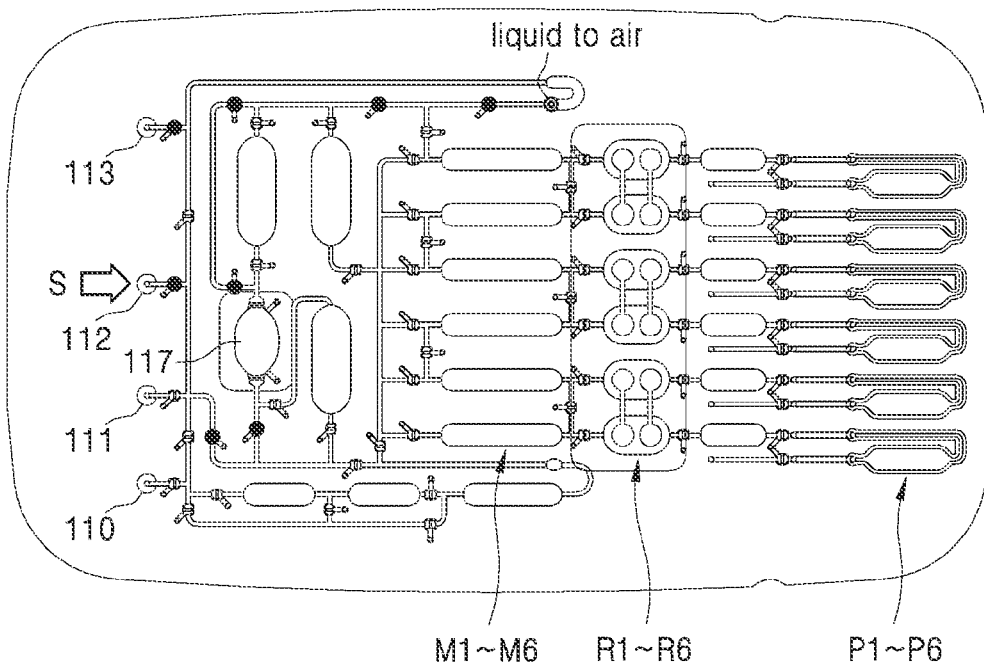
FIGS. 13A through 13T are plan views illustrating processes of performing operations according to the flowchart of FIG. 2 with valve operations used in the movement of a fluid in the microfluidic system.
Figure 13B:
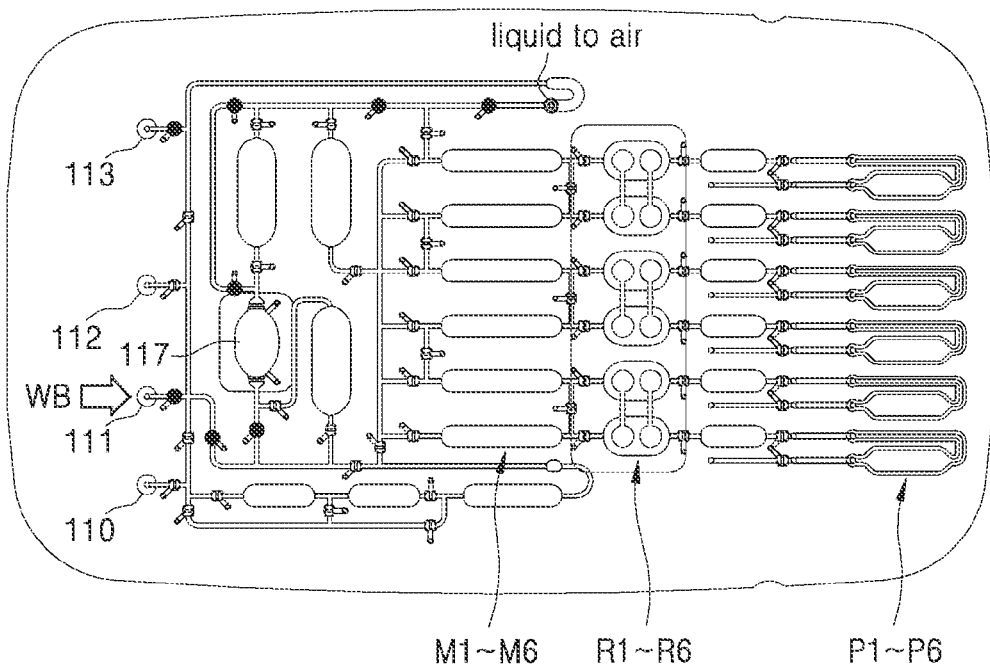
Figure 13C:
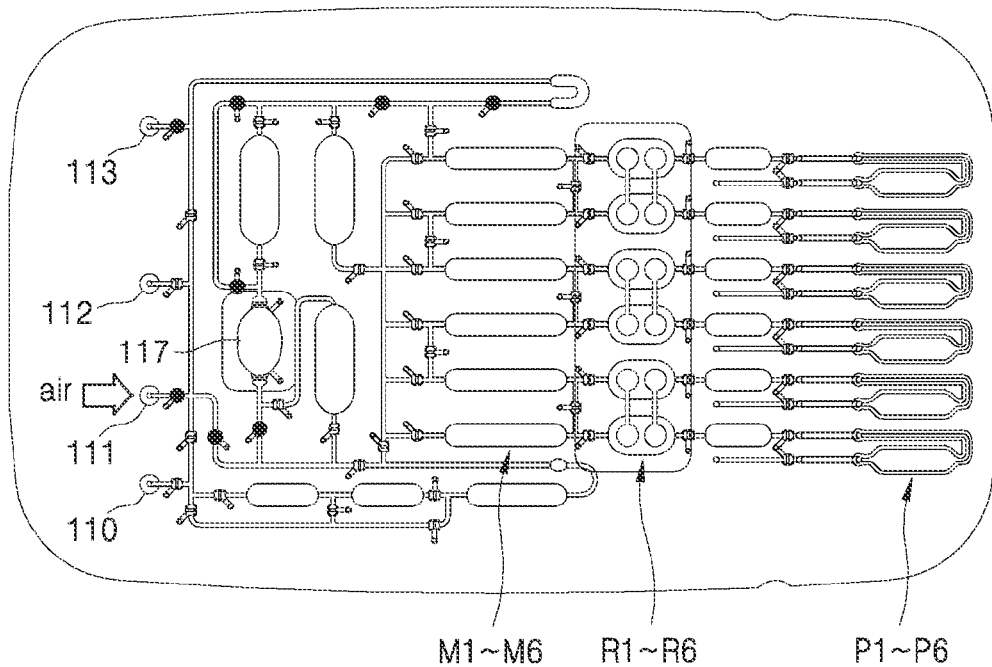
Figure 13D:
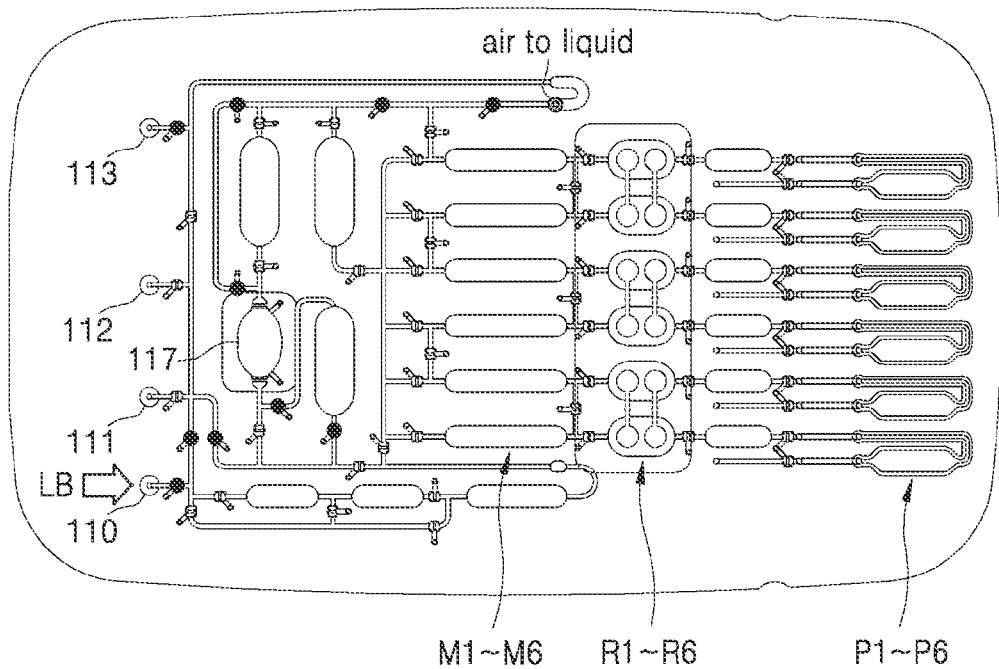
Figure 13E:
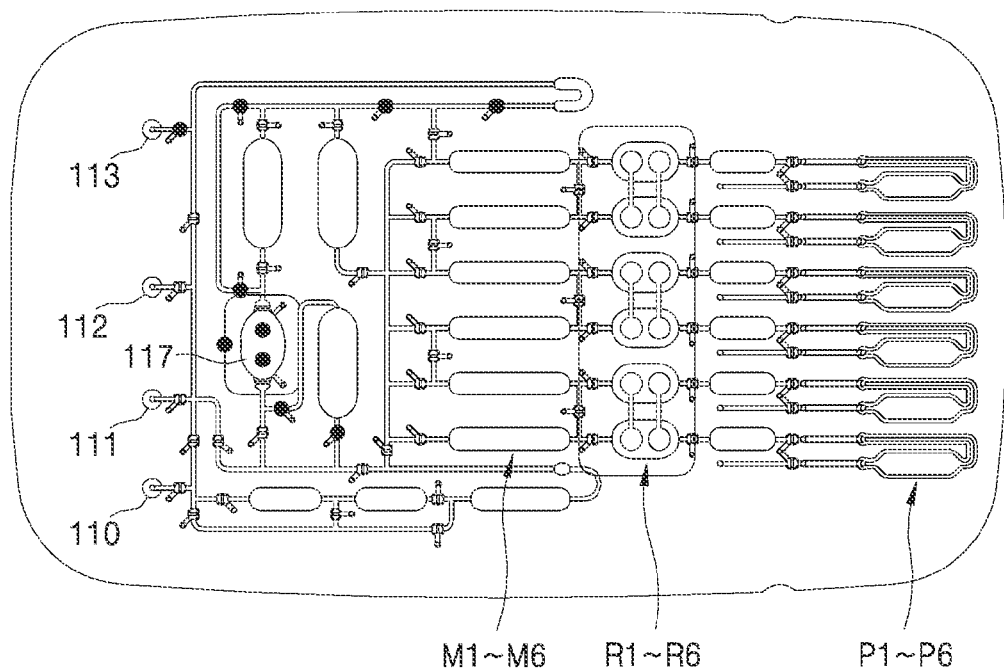
Figure 13F:
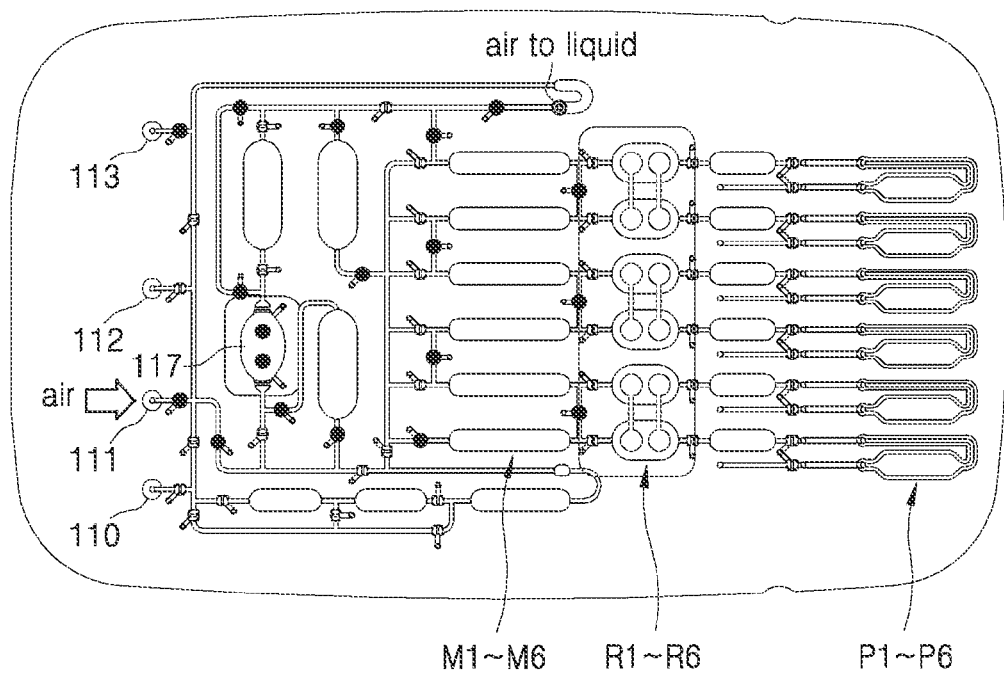
Figure 13G:
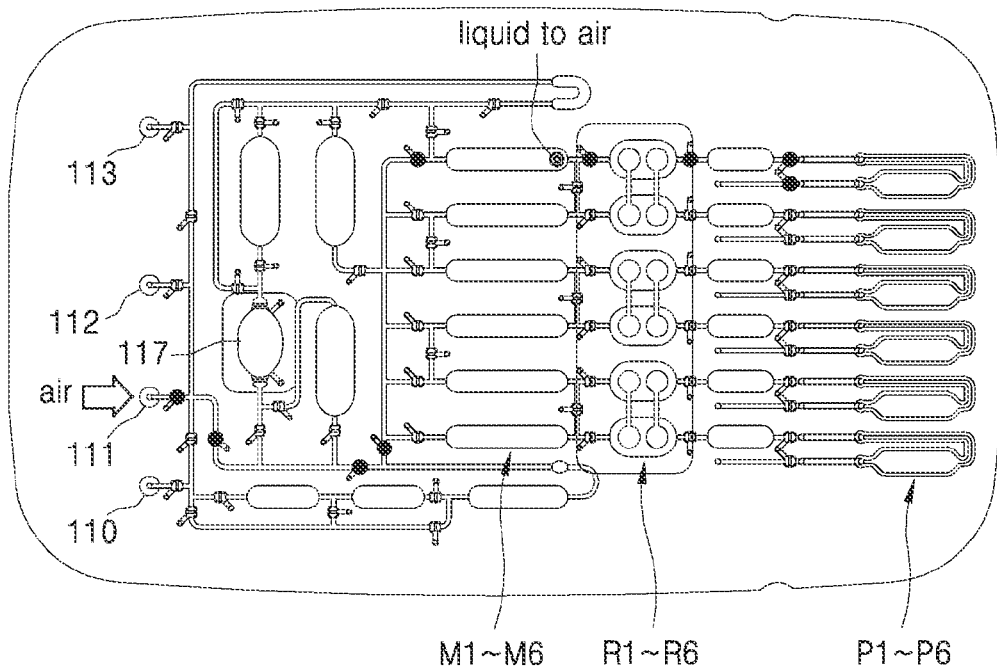
Figure 13H:
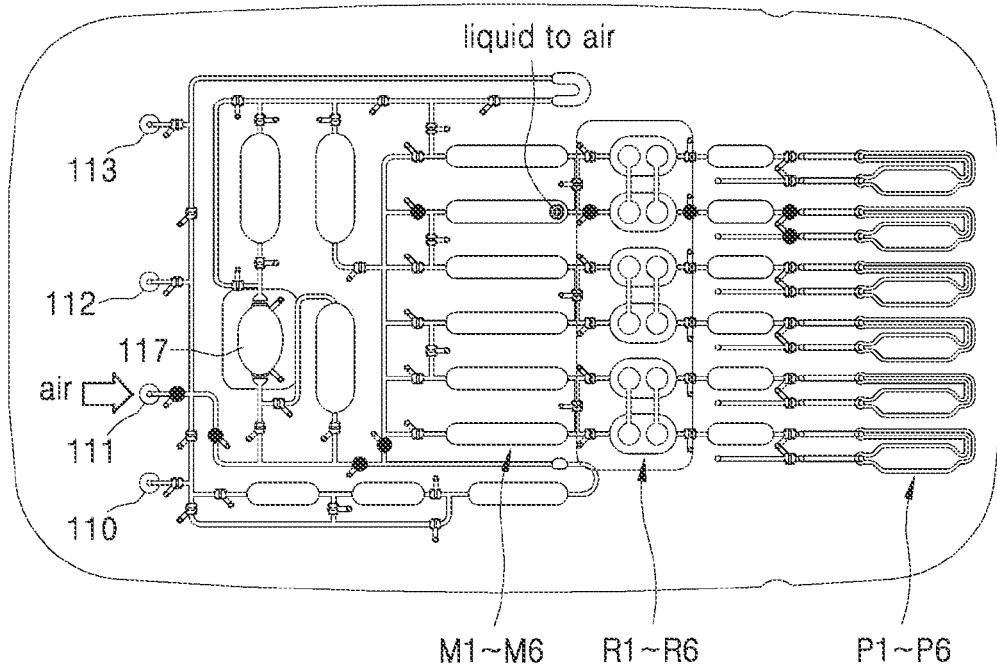
Figure 13I:
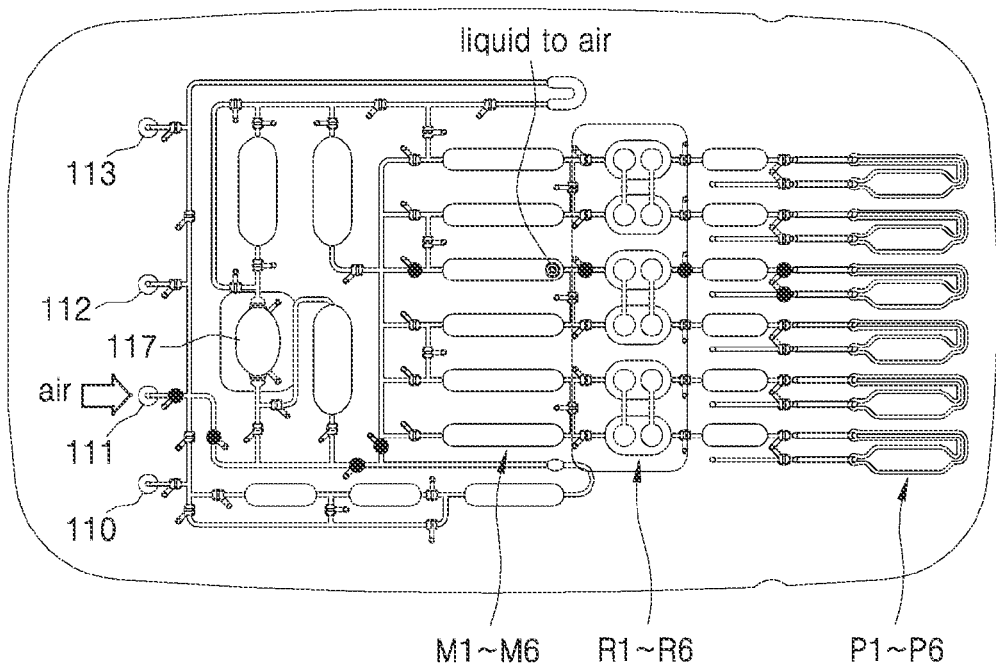
Figure 13J:
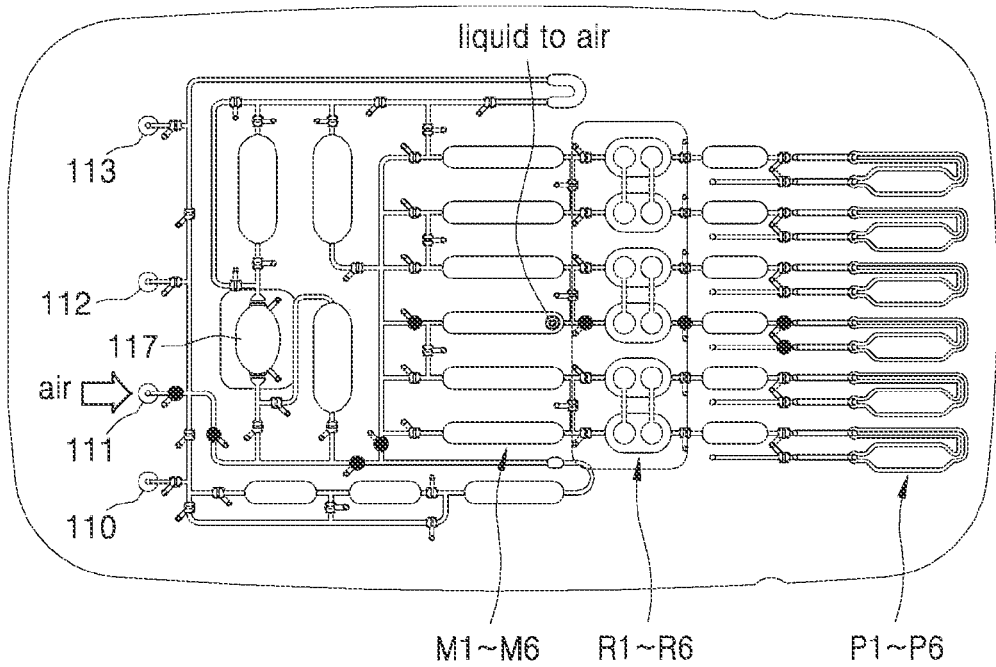
Figure 13K:
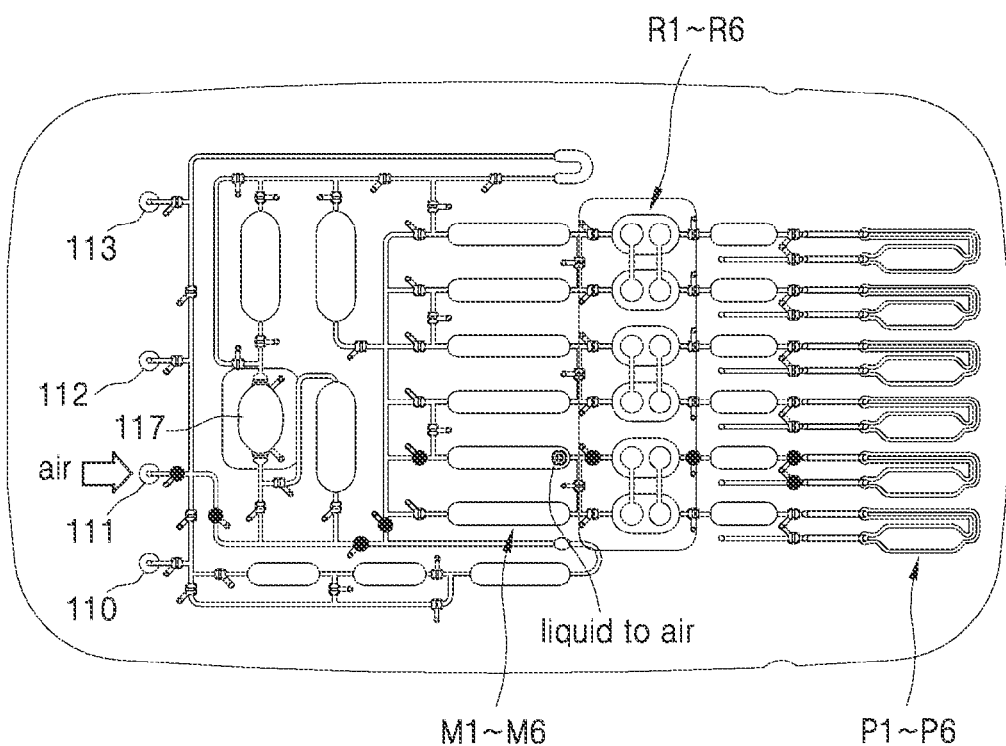
Figure 13L:
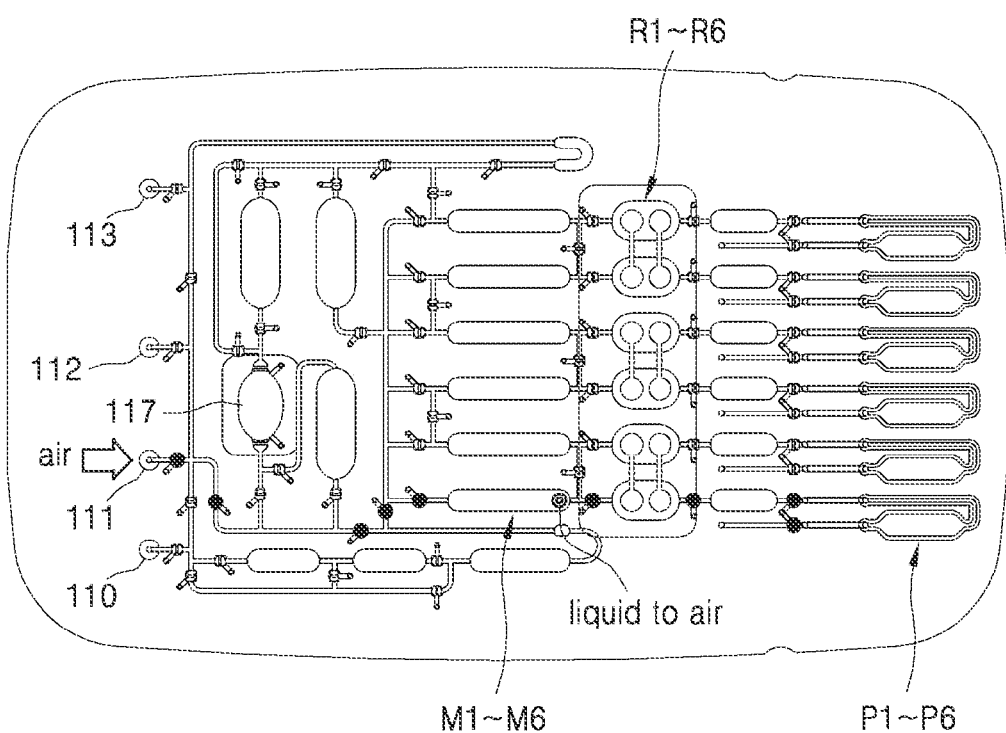
Figure 13M:
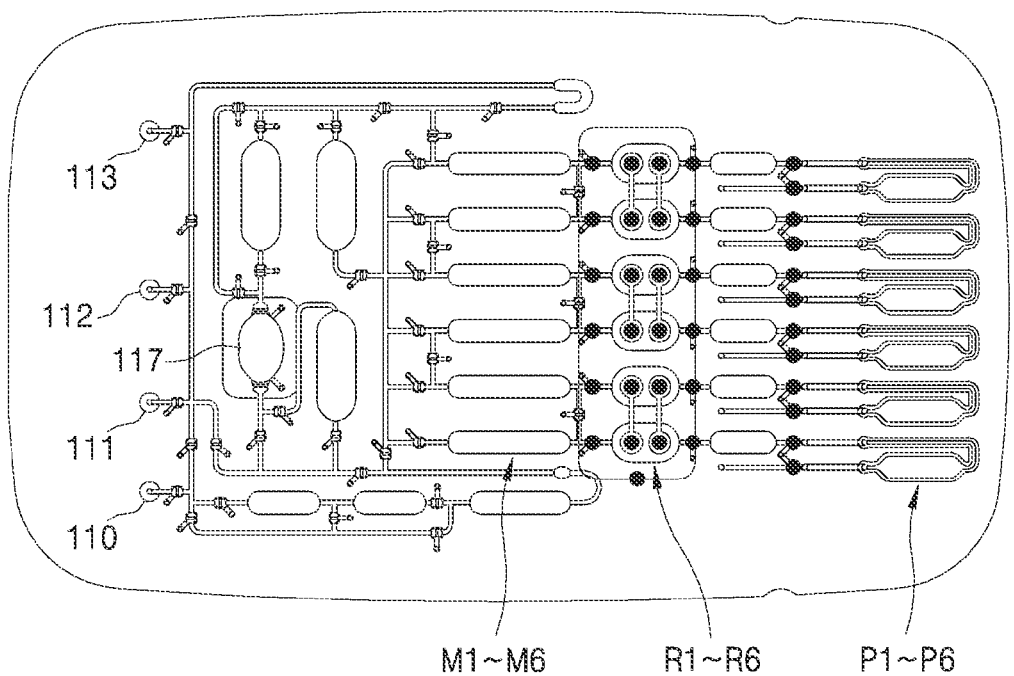
Figure 13N:
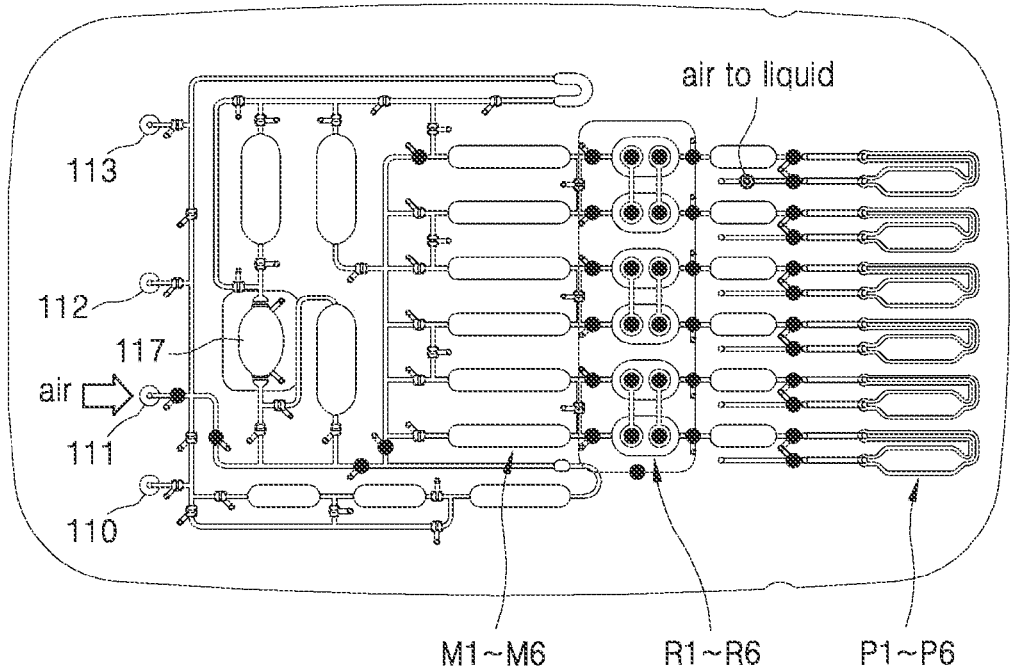
Figure 13O:
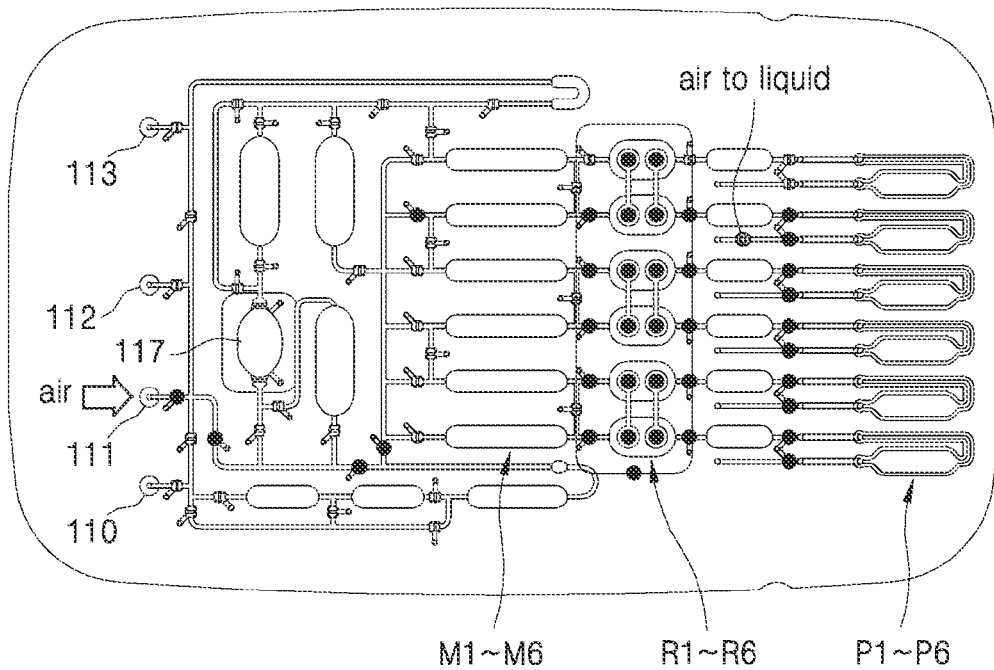
Figure 13P:
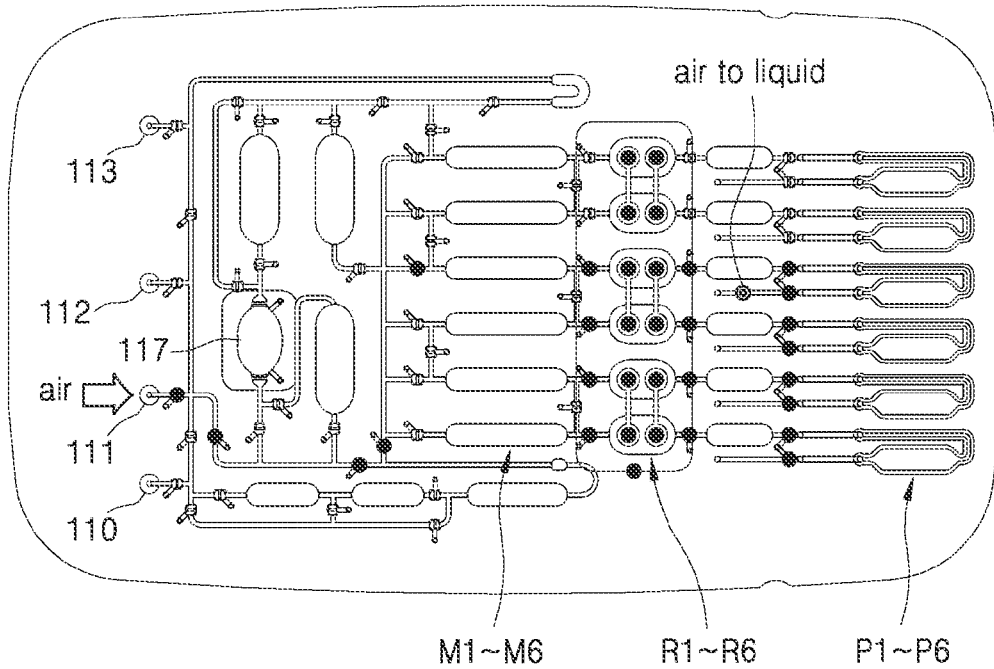
Figure 13Q:
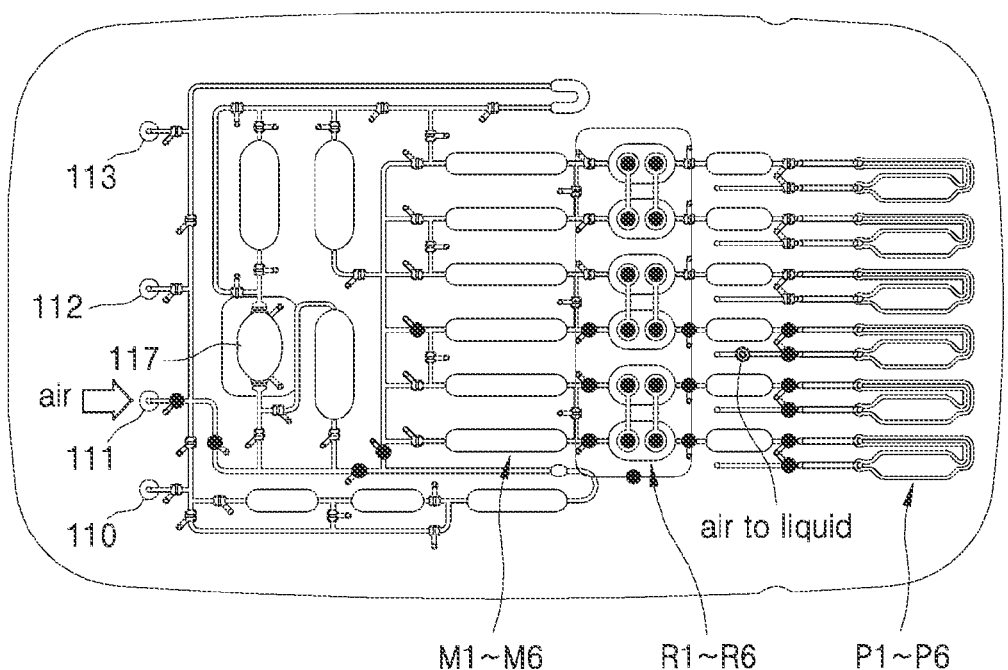
Figure 13R:
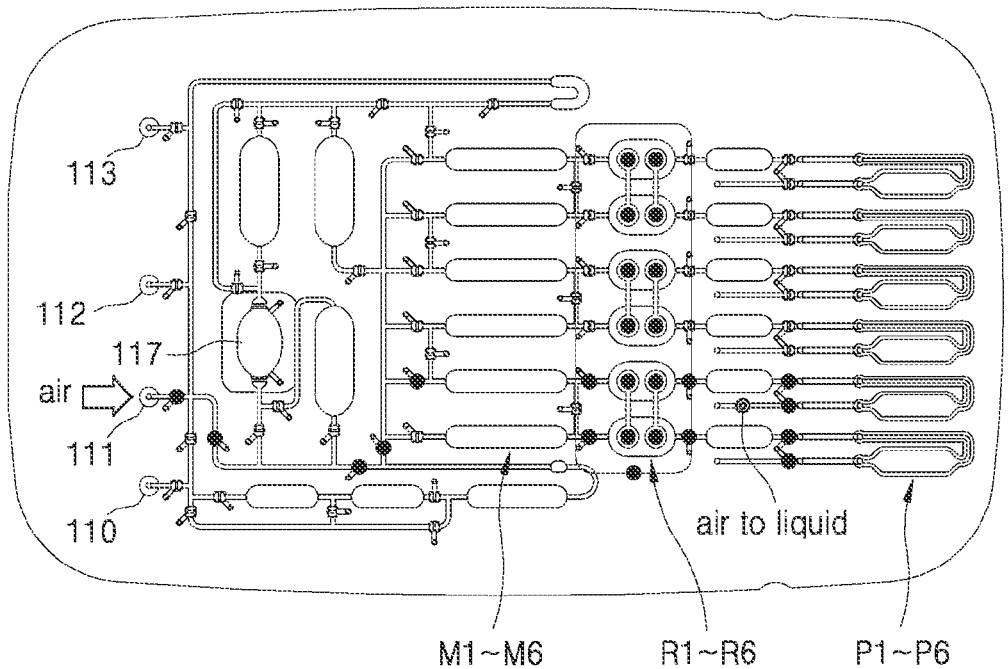
Figure 13S:
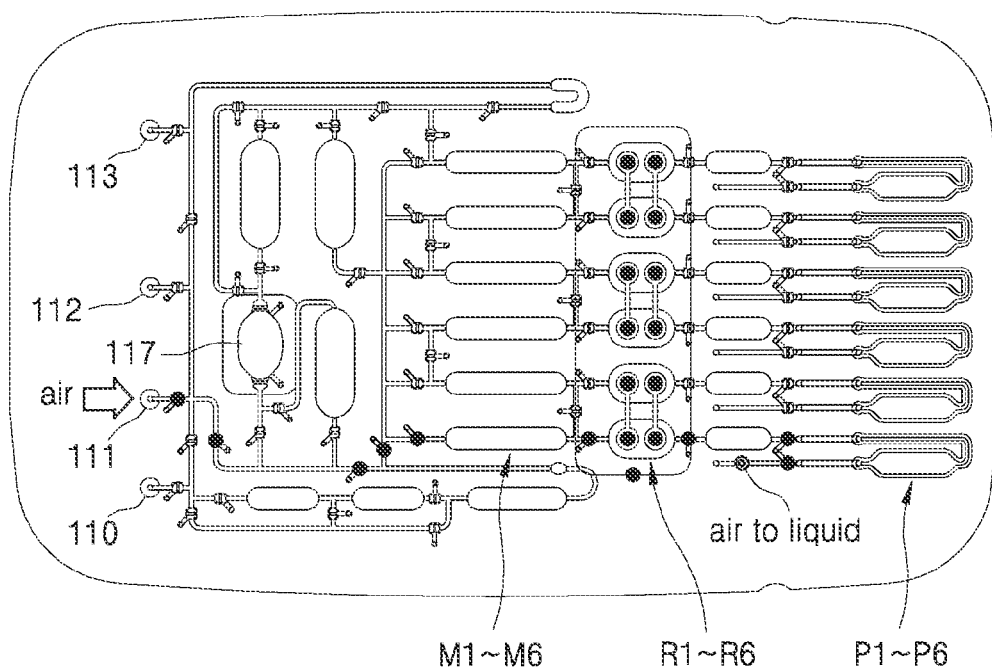
Figure 13T:
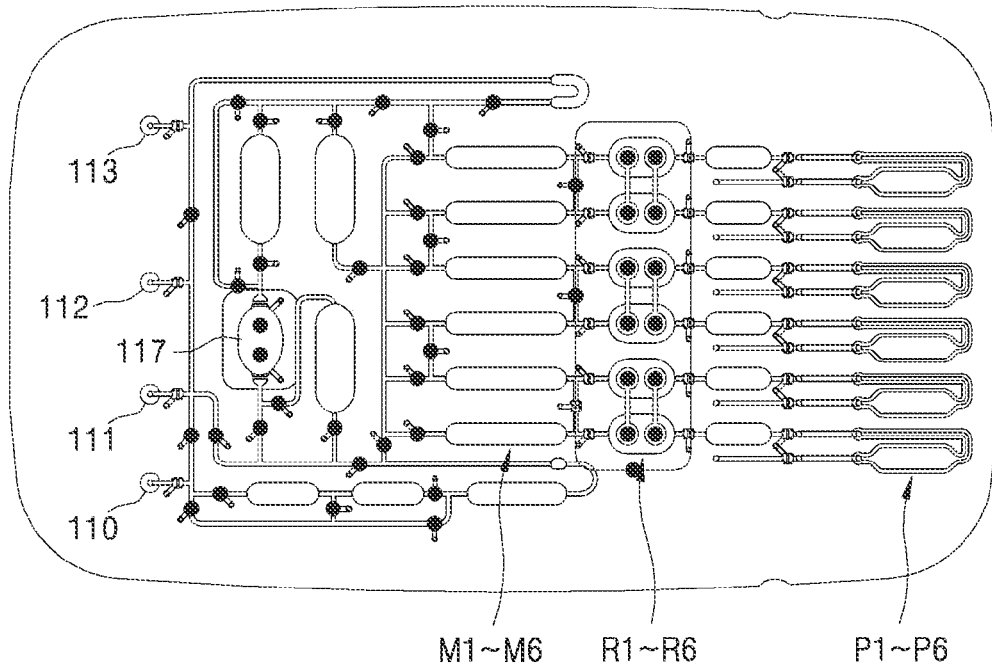

FIGS. 13A through 13T are plan views illustrating processes of performing operations according to the flowchart in FIG. 2 with valve operations required for the movement of a fluid in microfluidic system 1 according to an embodiment of the present invention.

The following exemplary processes illustrate using a microfluidic device described herein to capture cells from a sample, prepare a cell lysate containing nucleic acid (DNA), and determine the amount of DNA in the sample.

As illustrated in FIG. 13A, opened valves in microfluidic system 1 are represented as black dots (●). The valves are opened to inject about 1 ml of a sample S including the examination sample into binding-lysis chamber 117 through inlet 112 by using external pressure. In this process, cells are bound by the plurality of particles disposed in binding-lysis chamber 117 and the resulting solution is released toward outlet 113 to the waste chamber of reagent supply device 50. When the solution flows out from a solution sensing portion, which is represented as a double circle (◎), and the change from liquid to air is detected at the solution sensing portion, the above process is stopped and a subsequent process is performed.

As illustrated in FIG. 13B, the indicated valves are opened to inject about 0.5 ml of a washing buffer WB by using external pressure and the cells and the buffer are released toward outlet 113 to the waste chamber. When the solution flows out from the solution sensing portion and the change from liquid to air is detected at the solution sensing portion, the above process is stopped and a subsequent process is performed.

As illustrated in FIG. 13C, the indicated valves are opened to inject air through inlet 111 to dry the particles.

As illustrated in FIG. 13D, the indicated valves are opened to release a lysis buffer LB through inlet 110 to fill binding-lysis chamber 117. When the solution flows into the solution sensing portion and the change from air to liquid is detected, the above process is stopped and a subsequent process is performed.

As illustrated in FIG. 13E, the indicated valves are opened to prepare paths to vent and a portion of membrane part 30 corresponding to the bottom surface of binding-lysis chamber 117 is then vibrated. Membrane part 30 is vibrated at a frequency of about 5 Hz to perform cell lysis by allowing particle beating in binding-lysis chamber 117 to be maintained for about 5 minutes.

As illustrated in FIG. 13F, the indicated valves are opened to fill each of the six metering chambers M1-M6 in an amount of about 4 μl. When the solution flows in to the solution sensing portion and the change from air to liquid is detected, the above process is stopped and a subsequent process is performed.

As illustrated in FIG. 13G, the indicated valves are opened to push the cell lysate in metering chamber M1 into rehydration chamber R1. When the solution flows out from a solution sensing portion and the change from liquid to air is detected at the solution sensing portion, the above process is stopped and a subsequent process is performed.

As illustrated in FIG. 13H, the indicated valves are opened to push the cell lysate in metering chamber M2 into rehydration chamber R2. When the solution flows out from a solution sensing portion and the change from liquid to air is detected at the solution sensing portion, the above process is stopped and a subsequent process is performed.

As illustrated in FIG. 13I, the indicated valves are opened to push the cell lysate in metering chamber M3 into rehydration chamber R3. When the solution flows out from a solution sensing portion and the change from liquid to air is detected at the solution sensing portion, the above process is stopped and a subsequent process is performed.

As illustrated in FIG. 13J, the indicated valves are opened to push the cell lysate in metering chamber M4 into rehydration chamber R4. When the solution flows out from a solution sensing portion and the change from liquid to air is detected at the solution sensing portion, the above process is stopped and a subsequent process is performed.

As illustrated in FIG. 13K, the indicated valves are opened to push the cell lysate in metering chamber M5 into rehydration chamber R5. When the solution flows out from a solution sensing portion and the change from liquid to air is detected at the solution sensing portion, the above process is stopped and a subsequent process is performed.

As illustrated in FIG. 13L, the indicated valves are opened to push the cell lysate in metering chamber M6 into rehydration chamber R6. When the solution flows out from a solution sensing portion and the change from liquid to air is detected at the solution sensing portion, the above process is stopped and a subsequent process is performed.

As illustrated in FIG. 13M, the indicated valves are opened and a portion of membrane part 30 forming the bottom surfaces of rehydration chambers R1-R6 is vibrated. Membrane part 30 may be vibrated at a frequency of about 0.2 Hz and in this process PCR reagents in rehydration chambers R1-R6 are dissolved and mixed with the cell lysate to form a PCR mixture.

As illustrated in FIG. 13N, the indicated valves are opened while air is injected into inlet 111 to push the PCR mixture into PCR chamber P1. When the fluid passing a solution sensing portion changes from air to liquid as detected by the solution sensing portion, the above process is stopped and a subsequent process is performed.

As illustrated in FIG. 13O, the indicated valves are opened to push the PCR mixture into PCR chamber P2. When the fluid passing a solution sensing portion changes from air to liquid as detected by the solution sensing portion, the above process is stopped and a subsequent process is performed.

As illustrated in FIG. 13P, the indicated valves are opened to push the PCR mixture into PCR chamber P3. When the fluid passing a solution sensing portion changes from air to liquid as detected by the solution sensing portion, the above process is stopped and a subsequent process is performed.

As illustrated in FIG. 13Q, the indicated valves are opened to push the PCR mixture into PCR chamber P4. When the fluid passing a solution sensing portion changes from air to liquid as detected by the solution sensing portion, the above process is stopped and a subsequent process is performed.

As illustrated in FIG. 13R, the indicated valves are opened to push the PCR mixture into PCR chamber P5. When the fluid passing a solution sensing portion changes from air to liquid as detected by the solution sensing portion, the above process is stopped and a subsequent process is performed.

As illustrated in FIG. 13S, the indicated valves are opened to push the PCR mixture into PCR chamber P6. When the fluid passing a solution sensing portion changes from air to liquid as detected by the solution sensing portion, the above process is stopped and a subsequent process is performed.

As illustrated in FIG. 13T, a PCR is performed in a state in which the indicated valves are opened and only valves disposed at front ends of the PCR chambers P1-P6 are closed.

Thus, a process in which a sample as an examination target is distributed into the plurality of PCR chambers from the reagent supply device to undergo a PCR, i.e., a series of operations, such as cell binding, lysis, and mixing with a PCR reagent, may be accurately and reproducibly performed in an integrated system by using the foregoing microfluidic system 1.

When a sample to be examined is injected into the microfluidic system for analyzing nucleic acid, a series of operations occurs in which cells contained in the sample are captured and nucleic acid is extracted from the captured cells, and the nucleic acid is then mixed with a nucleic acid amplification reagent to perform a nucleic acid amplification reaction that is sequentially performed in the system. Thus, easy and accurate examination may be possible.

Because contamination from the outside, which may occur during a process after the extraction of nucleic acid from the sample to the nucleic acid amplification reaction, may be prevented, stable examination may be possible in comparison to the case in which each operation is performed in a separate system.

Furthermore, since a multiplex PCR, in which a PCR is performed by dividing a single sample into a plurality of the same chambers, may be possible, the microfluidic system may be suitable for the purpose of various clinical diagnoses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A microfluidic system for analyzing nucleic acid, the microfluidic system comprising:
   a reagent supply device including a sample chamber into which a sample can be injected, one or more reagent chambers for containing one or more reagents for extracting nucleic acid from the sample, and a waste chamber in which the used reagent can be discarded;
   a binding-lysis chamber in which cells are captured from the sample and lysed to form a cell lysate containing nucleic acid;
   a plurality of particles for cell binding disposed in the binding-lysis chamber;
   a plurality of rehydration chambers into which the cell lysate formed in the binding-lysis chamber can be distributed and mixed with a nucleic acid amplification reagent to form an amplification reaction mixture;
   a plurality of amplification chambers in which a nucleic acid amplification reaction is performed on the amplification reaction mixture introduced from the plurality of rehydration chambers; and
   a flow channel system including an outlet and a plurality of inlets connected to the reagent supply device and forming an integrated fluid flow between the binding-lysis chamber, the rehydration chambers, and the amplification chambers, and further comprising a fluid flow part comprising:
- a top surface comprising the plurality of inlets and the outlet, which are connected to the reagent supply device;
- a first through hole corresponding to the binding-lysis chamber;
- a plurality of second through holes corresponding to the plurality of rehydration chambers; and
- a bottom surface comprising a recessed groove pattern comprising a plurality of recessed grooves corresponding to the plurality of nucleic acid amplification chambers;
- a membrane part comprising an elastic membrane bonded to the bottom surface of the fluid flow part to form bottom surfaces of the binding-lysis chamber and the plurality of rehydration chambers;
- a pneumatic part bonded to a bottom surface of the membrane part and having a plurality of ports for applying pneumatic pressure to one or more predetermined positions of the membrane part; and
- a guide part for installing the reagent supply device, wherein the guide part is disposed on an upper portion of the fluid flow part and configured to align the plurality of inlets and the outlet of the fluid flow part with the plurality of chambers of the reagent supply part.

2. The microfluidic system of claim 1, wherein the plurality of reagent chambers comprises a lysis buffer chamber in which a lysis buffer can be injected, and a washing buffer chamber in which a washing buffer can be injected.

3. The microfluidic system of claim 2, wherein a destruction pattern, which is to be broken by external impact, is formed on each bottom surface of the sample chamber, the lysis buffer chamber, the washing buffer chamber, and the waste chamber.

4. The microfluidic system of claim 3, wherein the outlet and the plurality of inlets have a shape of a needle for applying an impact onto the destruction pattern.

5. The microfluidic system of claim 2, further comprising one or more metering chambers for quantifying an amount of the lysis buffer supplied from the lysis buffer chamber of the reagent supply device.

6. The microfluidic system of claim 1, further comprising one or more bubble trap chambers for removing bubbles generated during cell lysis in the binding-lysis chamber.

7. The microfluidic system of claim 1, wherein each of the plurality of rehydration chambers comprises two separated subchambers, and the nucleic acid amplification reagent is divided and disposed in the two subchambers.

8. The microfluidic system of claim 7, wherein, in each of the plurality of rehydration chambers, a sample including nucleic acid is disposed in one subchamber and a reagent including an enzyme is disposed in the other subchamber.

9. The microfluidic system of claim 8, wherein the sample including nucleic acid comprises one or more of a probe and a primer.

10. The microfluidic system of claim 7, wherein the nucleic acid amplification reagent is in a freeze-dried form.

11. The microfluidic system of claim 7, wherein a side of the subchamber has a curved shape and comprises a flow path therethrough with a width that is smallest at a center portion of the subchamber.

12. The microfluidic system of claim 1, further comprising a plurality of metering chambers for quantifying an amount of the cell lysate formed in the binding-lysis chamber and distributing the cell lysate into the plurality of rehydration chambers.

13. The microfluidic system of claim 1 further comprising:
- a binding-lysis chamber cover member that covers the first through hole at the top surface of the fluid flow part, wherein the cover member, the first through hole, and the membrane part define the binding lysis-chamber;
- one or more rehydration chamber cover members that cover the plurality of second through holes at the top surface of the fluid flow part, wherein each of the second through holes together with the cover member and membrane part define a rehydration chamber;
- a PCR film positioned on the bottom surface of the fluid flow part to cover the recessed groove pattern, wherein each of the recessed grooves together with the PCR film define a nucleic acid amplification chamber.

14. The microfluidic system of claim 1, wherein the bottom surface of the fluid flow part further comprises a microchannel providing the flow channel system, and a microvalve for preventing flow of a fluid passing along the microchannel when pneumatic pressure is applied from the pneumatic part.

15. The microfluidic system of claim 1, wherein a plurality of particles for cell binding is disposed in the first through hole.

16. The microfluidic system of claim 13, wherein the top surface of the fluid flow part comprises a bridge pattern having a shape recessed in the top surface of the fluid flow part that forms a path from the rehydration chamber to the nucleic acid amplification chamber by which the amplification reaction mixture can be transferred from the rehydration chamber to the nucleic amplification chamber.

17. The microfluidic system of claim 1, wherein the bottom surface of the fluid flow part further comprises a recess pattern,
the recess pattern providing one or more metering chambers for quantifying an amount of the lysis buffer supplied from the lysis buffer chamber of the reagent supply device on the bottom surface of the fluid flow part, one or more bubble trap chambers for removing bubbles generated during cell lysis in the binding-lysis chamber on the bottom surface of the fluid flow part, and a plurality of metering chambers for quantifying an amount of the cell lysate formed in the binding-lysis chamber and distributing the cell lysate into the plurality of rehydration chambers.

18. The microfluidic system of claim 1, wherein the fluid flow part is formed of a transparent polymer material.

19. The microfluidic system of claim 1, wherein the fluid flow part is formed of any one of polycarbonate (PC), polymethyl methacrylate (PMMA), polystyrene (PS), cyclic olefin copolymer (COC), polydimethylsiloxane (PDMS), and silicone.

20. The microfluidic system of claim 1, wherein the membrane part is formed of PDMS or silicone.

21. The microfluidic system of claim 1, wherein the pneumatic part is formed of a transparent polymer material.

22. A microfluidic system for analyzing nucleic acid, the microfluidic system comprising:
- a reagent supply device including a sample chamber into which a sample can be injected, one or more reagent chambers for containing one or more reagents for extracting nucleic acid from the sample, and a waste chamber in which the used reagent can be discarded;
- a binding-lysis chamber in which cells are captured from the sample and lysed to form a cell lysate containing nucleic acid;

a plurality of particles for cell binding disposed in the binding-lysis chamber;

a plurality of rehydration chambers into which the cell lysate formed in the binding-lysis chamber can be distributed and mixed with a nucleic acid amplification reagent to form an amplification reaction mixture;

a plurality of amplification chambers in which a nucleic acid amplification reaction is performed on the amplification reaction mixture introduced from the plurality of rehydration chambers; and a flow channel system including an outlet and a plurality of inlets connected to the reagent supply device and forming an integrated fluid flow between the binding-lysis chamber, the rehydration chambers, and the amplification chambers, and further comprising a fluid flow part comprising:

a top surface comprising the plurality of inlets and the outlet, which are connected to the reagent supply device;

a first through hole corresponding to the binding-lysis chamber;

a plurality of second through holes corresponding to the plurality of rehydration chambers; and a bottom surface comprising a recessed groove pattern comprising a plurality of recessed grooves corresponding to the plurality of nucleic acid amplification chambers;

a membrane part comprising an elastic membrane bonded to the bottom surface of the fluid flow part to form bottom surfaces of the binding-lysis chamber and the plurality of rehydration chambers; and a pneumatic part bonded to a bottom surface of the membrane part and having a plurality of ports for applying pneumatic pressure to one or more predetermined positions of the membrane part, wherein a single rehydration cover member covers the plurality of second through holes, and wherein the rehydration cover member comprises a plurality of protrusions at positions corresponding to the plurality of second through holes, and a plurality of grooves recessed in a predetermined shape on the plurality of protrusions and configured to hold a nucleic acid amplification reagent in a freeze-dried state.

23. The microfluidic system of claim 22, wherein a diameter of the protrusion is larger than a diameter of the second through hole, and sealing of the groove is performed by inserting the protrusion into the second through hole.

24. The microfluidic system of claim 23, wherein the protrusion is formed of a material having elasticity.

25. The microfluidic system of claim 22, wherein each of the plurality of grooves comprises two subgrooves separated from each other, and the nucleic acid amplification reagent is divided and disposed in the two subgrooves.

26. The microfluidic system of claim 25, wherein, in each of the plurality of grooves, a sample including a nucleic acid is disposed in one subgroove and a reagent including an enzyme is disposed in the other subgroove.

27. The microfluidic system of claim 26, wherein the sample including a nucleic acid comprises one or more of a probe and a primer.

28. The microfluidic system of claim 25, wherein a side of the subgroove has a curved shape and has a smallest width at a center portion thereof.

29. The microfluidic system of claim 28, wherein an external angle formed by corners of both sides of the subgroove at a position having the narrowest width is in a range of about 30 degrees to about 90 degrees.

30. A microfluidic system for analyzing nucleic acid, the microfluidic system comprising:

a reagent supply device including a sample chamber into which a sample can be injected, one or more reagent chambers for containing one or more reagents for extracting nucleic acid from the sample, and a waste chamber in which the used reagent can be discarded;

a binding-lysis chamber in which cells are captured from the sample and lysed to form a cell lysate containing nucleic acid;

a plurality of particles for cell binding disposed in the binding-lysis chamber;

a plurality of rehydration chambers into which the cell lysate formed in the binding-lysis chamber can be distributed and mixed with a nucleic acid amplification reagent to form an amplification reaction mixture;

a plurality of amplification chambers in which a nucleic acid amplification reaction is performed on the amplification reaction mixture introduced from the plurality of rehydration chambers; and a flow channel system including an outlet and a plurality of inlets connected to the reagent supply device and forming an integrated fluid flow between the binding-lysis chamber, the rehydration chambers, and the amplification chambers, and further comprising a fluid flow part comprising:

a top surface comprising the plurality of inlets and the outlet, which are connected to the reagent supply device;

a first through hole corresponding to the binding-lysis chamber;

a plurality of second through holes corresponding to the plurality of rehydration chambers; and a bottom surface comprising a recessed groove pattern comprising a plurality of recessed grooves corresponding to the plurality of nucleic acid amplification chambers;

a membrane part comprising an elastic membrane bonded to the bottom surface of the fluid flow part to form bottom surfaces of the binding-lysis chamber and the plurality of rehydration chambers;

a pneumatic part bonded to a bottom surface of the membrane part and having a plurality of ports for applying pneumatic pressure to one or more predetermined positions of the membrane part;

a binding-lysis chamber cover member that covers the first through hole at the top surface of the fluid flow part, wherein the cover member, the first through hole, and the membrane part define the binding lysis-chamber;

one or more rehydration chamber cover members that cover the plurality of second through holes at the top surface of the fluid flow part, wherein each of the second through holes together with the cover member and membrane part define a rehydration chamber; and a PCR film positioned on the bottom surface of the fluid flow part to cover the recessed groove pattern, wherein each of the recessed grooves together with the PCR film define a nucleic acid amplification chamber, wherein the top surface of the fluid flow part comprises a bridge pattern having a shape recessed in the top surface of the fluid flow part that forms a path from the rehydration chamber to the nucleic acid amplification chamber by which the amplification reaction mixture can be transferred from the rehydration chamber to the nucleic amplification chamber, and, wherein the bridge pattern comprises a plurality of subpatterns, and each of the plurality of subpatterns is provided by a hole penetrating the fluid flow part to face the membrane part, a hole penetrating the fluid flow part to face the PCR film, and a recessed bridge groove in the top surface of the fluid flow part connecting the two holes.

31. The microfluidic system of claim 30, wherein the system comprises a bridge cover entirely covering the plurality of subpatterns on the top surface of the fluid flow part.

* * * * *